(12) United States Patent
Orome et al.

(10) Patent No.: US 9,788,812 B2
(45) Date of Patent: Oct. 17, 2017

(54) NEEDLE GUIDE WITH SELECTABLE ASPECTS

(75) Inventors: Amir Orome, Sandy, UT (US); Matthew W. Bown, West Bountiful, UT (US); William R. Barron, Riverton, UT (US); Eric W. Lindekugel, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 769 days.

(21) Appl. No.: 13/531,406

(22) Filed: Jun. 22, 2012

(65) Prior Publication Data

US 2012/0330159 A1    Dec. 27, 2012

Related U.S. Application Data

(63) Continuation-in-part of application No. 13/335,587, filed on Dec. 22, 2011.
(Continued)

(51) Int. Cl.
*A61B 19/00* (2006.01)
*A61B 8/08* (2006.01)
(Continued)

(52) U.S. Cl.
CPC ............ *A61B 8/0841* (2013.01); *A61B 5/153* (2013.01); *A61B 5/15003* (2013.01);
(Continued)

(58) Field of Classification Search
CPC ..... A61B 8/00; A61B 17/3403; A61B 8/0841; A61B 8/0833; A61B 8/12;
(Continued)

(56) References Cited

U.S. PATENT DOCUMENTS

| 2,470,488 | A | * | 5/1949 | Friedrich Honerkamp ............... F24F 13/06 454/308 |
| 4,058,114 | A | | 11/1977 | Soldner |

(Continued)

FOREIGN PATENT DOCUMENTS

| CN | 3655315 | 6/2007 |
| DE | 2942405 A1 | 4/1981 |

(Continued)

OTHER PUBLICATIONS

PCT/US2011/066940 filed Dec. 22, 2011 International Search Report and Written Opinion dated Apr. 20, 2012.
(Continued)

*Primary Examiner* — Katherine M Shi
*Assistant Examiner* — Mohamed Gabr
(74) *Attorney, Agent, or Firm* — Rutan & Tucker, LLP

(57) ABSTRACT

A needle guide assembly for inserting a needle into the body of a patient in order to access a subcutaneous target, such as a vessel, is disclosed. In one embodiment, the needle guide assembly comprises a needle guide body that is configured to at least indirectly and removably attach to an image producing device, such as an ultrasound probe. The needle guide body defines at least first and second elongate guide channels. Each guide channel defines a unique insertion angle with respect to a longitudinal axis of the ultrasound probe. Further, each guide channel is configured to accept needles of differing gauges. In other embodiments other needle guide assemblies are disclosed that include multiple guide channels for inserting a needle at a variety of insertion angles into the patient's body. Related methods are also disclosed. In yet other embodiments, needle guide assemblies including needle stop features are disclosed.

18 Claims, 25 Drawing Sheets

Related U.S. Application Data

(60) Provisional application No. 61/426,297, filed on Dec. 22, 2010, provisional application No. 61/500,550, filed on Jun. 23, 2011.

(51) Int. Cl.

| | | |
|---|---|---|
| *A61B 17/34* | (2006.01) | |
| *A61B 5/15* | (2006.01) | |
| *A61M 5/46* | (2006.01) | |
| *A61B 5/153* | (2006.01) | |
| *A61B 5/155* | (2006.01) | |
| *A61B 8/00* | (2006.01) | |
| *A61B 10/02* | (2006.01) | |
| *A61M 5/32* | (2006.01) | |
| *A61B 6/12* | (2006.01) | |
| *A61M 5/42* | (2006.01) | |

(52) U.S. Cl.
CPC ........ *A61B 5/155* (2013.01); *A61B 5/150175* (2013.01); *A61B 5/150259* (2013.01); *A61B 5/150389* (2013.01); *A61B 5/150503* (2013.01); *A61B 5/150519* (2013.01); *A61B 5/150748* (2013.01); *A61B 5/150786* (2013.01); *A61B 5/150824* (2013.01); *A61B 8/4444* (2013.01); *A61B 17/3403* (2013.01); *A61M 5/46* (2013.01); *A61B 6/12* (2013.01); *A61B 8/085* (2013.01); *A61B 8/4411* (2013.01); *A61B 8/4422* (2013.01); *A61B 10/0233* (2013.01); *A61B 2017/3413* (2013.01); *A61M 5/3287* (2013.01); *A61M 5/427* (2013.01)

(58) Field of Classification Search
CPC .... A61B 2017/3413; A61B 2017/3405; A61B 2017/347; A61B 2017/3411; A61B 2017/00296; A61B 2090/378; A61B 2090/0814; A61B 90/11; A61B 10/0233; A61M 5/437; A61M 25/02; A61M 2025/024; A61M 2005/325
USPC .............. 600/439, 443, 461, 464, 459, 567; 606/130, 170; 604/165.01; 424/94.67
See application file for complete search history.

(56) References Cited

U.S. PATENT DOCUMENTS

| | | | |
|---|---|---|---|
| 4,108,165 A | 8/1978 | Kopp et al. | |
| 4,341,303 A | 7/1982 | Britt | |
| 4,346,717 A | 8/1982 | Haerten | |
| 4,363,326 A | 12/1982 | Kopel | |
| 4,402,324 A | 9/1983 | Lindgren et al. | |
| 4,408,611 A | 10/1983 | Enjoji | |
| 4,469,106 A | 9/1984 | Harui | |
| 4,497,325 A | 2/1985 | Wedel | |
| 4,548,210 A | 10/1985 | Enjoji et al. | |
| 4,576,175 A | 3/1986 | Epstein | |
| 4,582,326 A * | 4/1986 | Alsip .................. | A63F 3/00094 273/271 |
| 4,608,989 A | 9/1986 | Drue | |
| 4,635,644 A | 1/1987 | Yagata | |
| 4,662,870 A | 5/1987 | Augustine et al. | |
| 4,681,103 A | 7/1987 | Boner et al. | |
| 4,723,544 A | 2/1988 | Moore et al. | |
| 4,742,829 A | 5/1988 | Law et al. | |
| 4,838,506 A | 6/1989 | Cooper | |
| 4,877,033 A | 10/1989 | Seitz, Jr. | |
| 4,883,059 A | 11/1989 | Stedman et al. | |
| 4,898,178 A | 2/1990 | Wedel | |
| 4,899,756 A | 2/1990 | Sonek | |
| 4,911,173 A | 3/1990 | Terwilliger | |
| 4,979,748 A * | 12/1990 | Danielak ............ | A63F 3/00094 273/241 |
| 5,052,396 A | 10/1991 | Wedel et al. | |
| 5,076,279 A | 12/1991 | Arenson et al. | |
| 5,100,387 A | 3/1992 | Ng | |
| 5,138,748 A * | 8/1992 | Welles ....................... | 24/30.5 S |
| 5,235,987 A | 8/1993 | Wolfe | |
| 5,265,614 A | 11/1993 | Hayakawa et al. | |
| 5,280,427 A | 1/1994 | Magnusson et al. | |
| 5,427,108 A | 6/1995 | Bollinger | |
| D362,064 S | 9/1995 | Smick | |
| 5,494,039 A | 2/1996 | Onik et al. | |
| 5,623,931 A | 4/1997 | Wung et al. | |
| 5,758,650 A | 6/1998 | Miller et al. | |
| D399,971 S | 10/1998 | Scherer | |
| 5,911,707 A | 6/1999 | Wolvek et al. | |
| D412,032 S | 7/1999 | Mikula-Curtis et al. | |
| 5,924,992 A | 7/1999 | Park et al. | |
| 5,941,889 A | 8/1999 | Cermak | |
| 6,050,954 A | 4/2000 | Mittermeier | |
| D424,693 S | 5/2000 | Pruter | |
| 6,083,169 A | 7/2000 | Hansen | |
| 6,095,981 A | 8/2000 | McGahan | |
| D434,850 S | 12/2000 | Balestracci | |
| 6,203,499 B1 | 3/2001 | Imling et al. | |
| 6,283,942 B1 | 9/2001 | Staehlin et al. | |
| 6,296,614 B1 | 10/2001 | Pruter | |
| 6,361,499 B1 | 3/2002 | Bates et al. | |
| 6,368,280 B1 | 4/2002 | Cermak et al. | |
| 6,379,307 B1 | 4/2002 | Filly et al. | |
| 6,425,871 B1 | 7/2002 | Jaggi | |
| 6,475,152 B1 | 11/2002 | Kelly, Jr. et al. | |
| 6,485,426 B2 | 11/2002 | Sandhu | |
| 6,612,990 B1 | 9/2003 | Pruter | |
| 6,695,786 B2 | 2/2004 | Wang et al. | |
| 6,743,177 B2 | 6/2004 | Ito et al. | |
| 6,758,817 B1 | 7/2004 | Pruter et al. | |
| 6,814,704 B2 | 11/2004 | Weilandt | |
| 6,840,954 B2 | 1/2005 | Dietz et al. | |
| 6,877,352 B1 * | 4/2005 | Schlereth ......... | A61B 17/06004 29/282 |
| 6,884,219 B1 | 4/2005 | Pruter | |
| 6,908,433 B1 | 6/2005 | Pruter | |
| 7,022,082 B2 | 4/2006 | Sonek | |
| 7,087,024 B1 * | 8/2006 | Pruter ............................ | 600/461 |
| 7,322,990 B1 | 1/2008 | Mark et al. | |
| 7,351,205 B2 | 4/2008 | Szczech et al. | |
| 7,452,331 B1 * | 11/2008 | Pruter .................. | A61B 8/0833 600/433 |
| 7,588,541 B2 | 9/2009 | Floyd et al. | |
| 7,635,336 B1 | 12/2009 | Pruter | |
| 7,670,294 B2 | 3/2010 | Kisen et al. | |
| 7,691,066 B2 | 4/2010 | Kosaku | |
| D625,802 S | 10/2010 | Choi et al. | |
| D625,805 S | 10/2010 | Hereford | |
| 7,837,627 B1 | 11/2010 | Pruter | |
| D629,898 S | 12/2010 | Bigelow | |
| D630,731 S | 1/2011 | Schmutzer et al. | |
| 7,909,815 B2 | 3/2011 | Whitmore, III et al. | |
| 7,976,469 B2 | 7/2011 | Bonde et al. | |
| D649,245 S | 11/2011 | Klebs et al. | |
| 8,073,529 B2 | 12/2011 | Cermak et al. | |
| 8,075,495 B2 | 12/2011 | Andreyko et al. | |
| 8,118,743 B2 | 2/2012 | Park et al. | |
| D655,813 S | 3/2012 | Row et al. | |
| 8,137,281 B2 | 3/2012 | Huang et al. | |
| D659,825 S | 5/2012 | Dillard, III | |
| D672,460 S | 12/2012 | Baid | |
| 8,430,889 B2 | 4/2013 | Zeng et al. | |
| D683,019 S | 5/2013 | Shahidi Bonjar | |
| 8,496,593 B2 | 7/2013 | Park et al. | |
| 8,523,824 B2 | 9/2013 | Teirstein et al. | |
| 8,641,620 B2 | 2/2014 | Lasser et al. | |
| 8,647,280 B2 | 2/2014 | Ooishi et al. | |
| 8,696,583 B2 | 4/2014 | Ohgishi et al. | |
| 8,696,585 B2 | 4/2014 | Addison et al. | |
| 8,708,916 B2 | 4/2014 | Okuno | |
| 8,740,800 B2 | 6/2014 | Wakabayashi et al. | |
| 8,747,324 B1 | 6/2014 | Pruter et al. | |

(56) References Cited

U.S. PATENT DOCUMENTS

| | | | |
|---|---|---|---|
| D710,995 S | 8/2014 | Shirley et al. | |
| 8,795,183 B2 | 8/2014 | Siebrecht et al. | |
| 8,808,186 B2 | 8/2014 | Fruland et al. | |
| D727,495 S | 4/2015 | Bown et al. | |
| 2002/0123689 A1 | 9/2002 | Furia | |
| 2002/0133079 A1 | 9/2002 | Sandhu | |
| 2003/0144627 A1 | 7/2003 | Woehr et al. | |
| 2003/0195425 A1 | 10/2003 | Ito | |
| 2004/0133111 A1 | 7/2004 | Szczech et al. | |
| 2005/0059891 A1 | 3/2005 | Kosaku | |
| 2005/0113816 A1 | 5/2005 | Whitmore et al. | |
| 2005/0143753 A1 | 6/2005 | Whitmore et al. | |
| 2005/0267373 A1 | 12/2005 | Lee | |
| 2006/0129046 A1 | 6/2006 | Stevens et al. | |
| 2006/0150876 A1 | 7/2006 | Green et al. | |
| 2006/0241477 A1 | 10/2006 | Sasady et al. | |
| 2007/0016781 A1 | 1/2007 | Asokan et al. | |
| 2007/0038113 A1 | 2/2007 | Oonuki et al. | |
| 2007/0073155 A1 | 3/2007 | Park et al. | |
| 2007/0078346 A1 | 4/2007 | Park et al. | |
| 2007/0112272 A1 | 5/2007 | Park et al. | |
| 2007/0167817 A1 | 7/2007 | Huang et al. | |
| 2007/0276241 A1 | 11/2007 | Park et al. | |
| 2007/0276253 A1 | 11/2007 | Park et al. | |
| 2007/0282205 A1 | 12/2007 | Furia | |
| 2008/0033454 A1 | 2/2008 | Lukoschek et al. | |
| 2008/0300491 A1 | 12/2008 | Bonde et al. | |
| 2009/0143684 A1* | 6/2009 | Cermak | A61B 8/0841 600/461 |
| 2009/0171219 A1* | 7/2009 | Uchibori | 600/461 |
| 2009/0247876 A1 | 10/2009 | Cannon, Jr. et al. | |
| 2009/0266957 A1 | 10/2009 | Cermak | |
| 2009/0270722 A1 | 10/2009 | Floyd et al. | |
| 2009/0275833 A1 | 11/2009 | Ikeda et al. | |
| 2010/0010475 A1* | 1/2010 | Teirstein et al. | 604/528 |
| 2010/0041990 A1 | 2/2010 | Schlitt et al. | |
| 2010/0081920 A1 | 4/2010 | Whitmore, III et al. | |
| 2010/0106056 A1 | 4/2010 | Norris | |
| 2010/0160787 A1* | 6/2010 | Gorzitze | 600/461 |
| 2010/0228131 A1 | 9/2010 | Oonuki et al. | |
| 2010/0247513 A1 | 9/2010 | Agee et al. | |
| 2010/0312121 A1 | 12/2010 | Guan | |
| 2011/0028847 A1 | 2/2011 | Whitmore, III et al. | |
| 2012/0165679 A1 | 6/2012 | Orome et al. | |
| 2013/0150714 A1 | 6/2013 | Howlett et al. | |
| 2013/0245452 A1 | 9/2013 | Gorzitze | |
| 2015/0025315 A1 | 1/2015 | Nishina et al. | |
| 2015/0112200 A1 | 4/2015 | Oberg et al. | |

FOREIGN PATENT DOCUMENTS

| | | |
|---|---|---|
| EP | 1709919 A1 | 10/2006 |
| JP | 01097440 A | 4/1989 |
| JP | 03173542 A | 7/1991 |
| JP | 11128237 A | 5/1999 |
| JP | 21161683 | 6/2001 |
| JP | 21340334 | 12/2001 |
| JP | 23299654 | 10/2003 |
| JP | 23334191 | 11/2003 |
| JP | 2005-034273 A | 2/2005 |
| JP | D1268564 | 4/2006 |
| JP | 2009-153831 A | 7/2009 |
| JP | 2010-115246 A | 5/2010 |
| WO | 9610958 A2 | 4/1996 |
| WO | 0019906 | 4/2000 |
| WO | 0040155 | 7/2000 |
| WO | 0040155 A1 | 7/2000 |
| WO | 03094701 A2 | 11/2003 |
| WO | 2004021898 A1 | 3/2004 |
| WO | 2006060657 A2 | 6/2006 |
| WO | 2007027511 A2 | 3/2007 |
| WO | 2007040172 A1 | 4/2007 |
| WO | 2007110076 A1 | 10/2007 |
| WO | 2008024515 A2 | 2/2008 |
| WO | 2009073653 A1 | 6/2009 |
| WO | 2009090230 A1 | 7/2009 |
| WO | 2010080637 A1 | 7/2010 |
| WO | 2010084322 A1 | 7/2010 |
| WO | 2012088458 | 6/2012 |
| WO | 2012178109 | 12/2012 |
| WO | 2013054168 A2 | 4/2013 |
| WO | 2015100332 A1 | 7/2015 |

OTHER PUBLICATIONS

CN 201180067467.2 filed Aug. 13, 2013 First Office Action dated Sep. 4, 2014.

PCT/US2009/068828 filed Dec. 18, 2009 International Preliminary Report on Patentability dated Jun. 21, 2011.

PCT/US2009/068828 filed Dec. 18, 2009 Search Report dated Mar. 3, 2010.

PCT/US2009/068828 filed Dec. 18, 2009 Written Opinion dated Mar. 3, 2010.

PCT/US2011/066940 filed Dec. 22, 2011 International Preliminary Report on Patentability dated Jul. 4, 2013.

PCT/US2012/043877 filed Jun. 22, 2012 International Search Report and Written Opinion dated Sep. 24, 2012.

U.S. Appl. No. 12/642,456, filed Dec. 18, 2009 Final Office Action dated Nov. 23, 2012.

U.S. Appl. No. 12/642,456, filed Dec. 18, 2009 Non-Final Office Action dated Jul. 2, 2012.

U.S. Appl. No. 12/642,456, filed Dec. 18, 2009 Notice of Allowance dated Jul. 12, 2013.

U.S. Appl. No. 13/335,587, filed Dec. 22, 2011 Final Office Action dated Jul. 28, 2014.

U.S. Appl. No. 13/335,587, filed Dec. 22, 2011 Non-Final Office Action dated Mar. 12, 2014.

U.S. Appl. No. 13/886,196, filed May 2, 2013 Advisory Action dated Jun. 13, 2014.

U.S. Appl. No. 13/886,196, filed May 2, 2013 Final Office Action dated Apr. 10, 2014.

U.S. Appl. No. 13/886,196, filed May 2, 2013 Final Office Action dated Dec. 22, 2014.

U.S. Appl. No. 13/886,196, filed May 2, 2013 Non-Final Office Action dated Dec. 19, 2013.

U.S. Appl. No. 13/886,196, filed May 2, 2013 Non-Final Office Action dated Jul. 25, 2014.

EP 11 850 516.3 filed Jul. 19, 2013 Extended European Search Report dated Mar. 4, 2015.

EP 12 803 493.1 filed Jan. 15, 2014 Extended European Search Report dated Mar. 5, 2015.

U.S. Appl. No. 13/335,587, filed Dec. 22, 2011 Non-Final Office Action dated Feb. 2, 2015.

CN 201180067467.2 filed Aug. 13, 2013 second Office Action dated Apr. 30, 2015.

CN 201280030885.9 filed Dec. 23, 2013 First Office Action dated Mar. 3, 2015.

PCT/US2014/072168 filed Dec. 23, 2014 International Search Report and Written Opinion dated Apr. 16, 2015.

U.S. Appl. No. 13/335,587, filed Dec. 22, 2011 Final Office Action dated Jul. 8, 2015.

U.S. Appl. No. 13/886,196, filed May 2, 2013 Examiner's Answer dated Nov. 3, 2015.

CN 201280030885.9 filed Dec. 23, 2013 Second Office Action dated Nov. 4, 2015.

U.S. Appl. No. 13/335,587, filed Dec. 22, 2011 Examiner's Answer dated May 16, 2016.

CN 201180067467.2 filed Aug. 13, 2013 Third Office Action dated Oct. 28, 2015.

U.S. Appl. No. 29/493,150, filed Jun. 5, 2014 Notice of Allowance dated Oct. 29, 2015.

CN 201280030885.9 filed Dec. 23, 2013 Third Office Action dated May 5, 2016.

JP 2013-546435 filed Jun. 6, 2013 Office Action dated Aug. 29, 2016.

JP 2014-517229 filed Dec. 20, 2013 First Office Action dated May 24, 2016.

(56) References Cited

OTHER PUBLICATIONS

JP 2014-517229 filed Dec. 20, 2013 Notice of Allowance dated Oct. 3, 2016.
U.S. Appl. No. 14/581,019, filed Dec. 23, 2014 Non-Final Office Action dated Apr. 12, 2017.
EP 14875859.2 filed Jun. 9, 2016 Extended European Search Report dated Jul. 31, 2017.

* cited by examiner

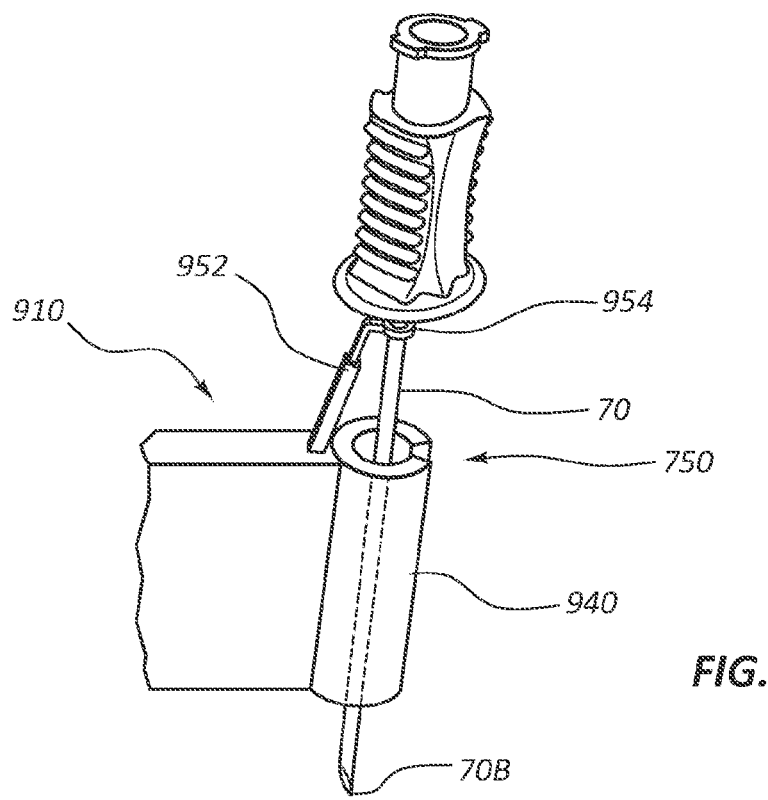
FIG. 27A
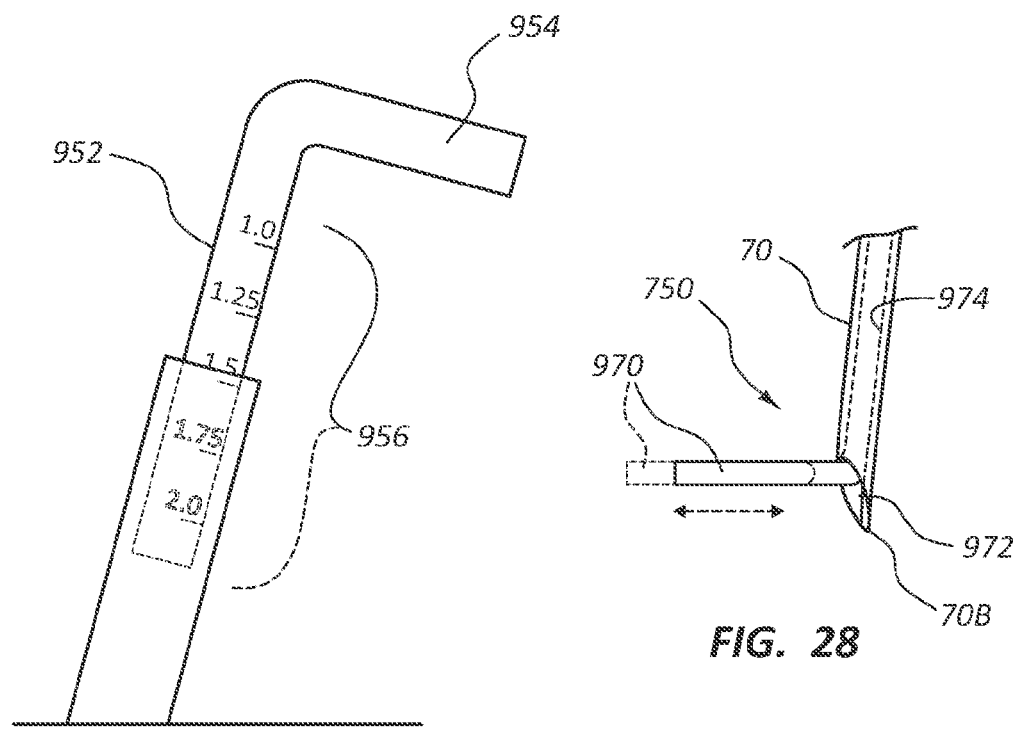
FIG. 27B
FIG. 28

NEEDLE GUIDE WITH SELECTABLE ASPECTS

CROSS-REFERENCE TO RELATED APPLICATIONS

This application is a continuation-in-part of U.S. patent application Ser. No. 13/335,587, filed Dec. 22, 2011, and titled "Selectable Angle Needle Guide," which claims the benefit of U.S. Provisional Patent Application No. 61/426,297, filed Dec. 22, 2010, and titled "Selectable Angle Needle Guide." This application also claims the benefit of U.S. Provisional Patent Application No. 61/500,550, filed Jun. 23, 2011, and titled "Needle Guide with Selectable Aspects." Each of the aforementioned applications is incorporated herein by reference in its entirety.

BRIEF SUMMARY

Briefly summarized, embodiments of the present invention are directed to a needle guide assembly for inserting a needle into the body of a patient in order to access a subcutaneous target, such as a vessel. In one embodiment, the needle guide assembly comprises a needle guide body that is configured to at least indirectly and removably attach to an image producing device, such as an ultrasound probe. The needle guide body defines at least first and second elongate guide channels. Each guide channel defines a unique insertion angle with respect to a longitudinal axis of the ultrasound probe. Further, each guide channel is configured to accept needles of differing gauges.

In other embodiments, other needle guide assemblies are disclosed that include multiple guide channels for inserting a needle at a variety of insertion angles into the patient's body. Related methods are also disclosed. In yet other embodiments, needle guide assemblies including needle stop features are disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 27A and 27B are various views of a needle stop feature according to one embodiment;

FIG. 28 is a view of a needle stop feature according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale. It is to be understood that the words "including," "has," and "having," as used herein, including the claims, shall have the same meaning as the word "comprising."

For clarity it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. Also, the words "including," "has," and "having," as used herein, including the claims, shall have the same meaning as the word "comprising."

Embodiments of the present invention are generally directed to a needle guide assembly for guiding a needle or other elongate implement into a body of a patient. In one embodiment, the needle guide is removably attached in a direct or indirect manner to an ultrasound probe so as to enable insertion of the needle via the needle guide assembly while an intended subcutaneous target of the needle is being imaged by the ultrasound probe. Further, in one embodiment, the needle guide assembly includes multiple differently angled needle guide channels that are selectable by a user to enable the needle to be directed at a desired angle into the patient's body toward the subcutaneous target. Thus, the ability to direct a needle at a variety of angles with a single guide assembly is achieved.

FIGS. 1A-1D depict one example of a needle guide assembly, generally designated at 10, according to one embodiment. As shown, the needle guide assembly 10 includes a body 12 for attaching the assembly to an image producing device, as will be described further below. In one embodiment, the image producing device includes a hand-held probe of an ultrasound imaging device, though other imaging devices can also be utilized, such x-ray and MRI-based systems, for example. Optionally, the needle guide assembly can be attached to other components in addition to image producing devices. The needle guide body 12 in the present embodiment includes thermoplastic, but in other embodiments other materials can be employed, including other types of plastic, metals, metal alloys, ceramics, etc.

Figure 1A:
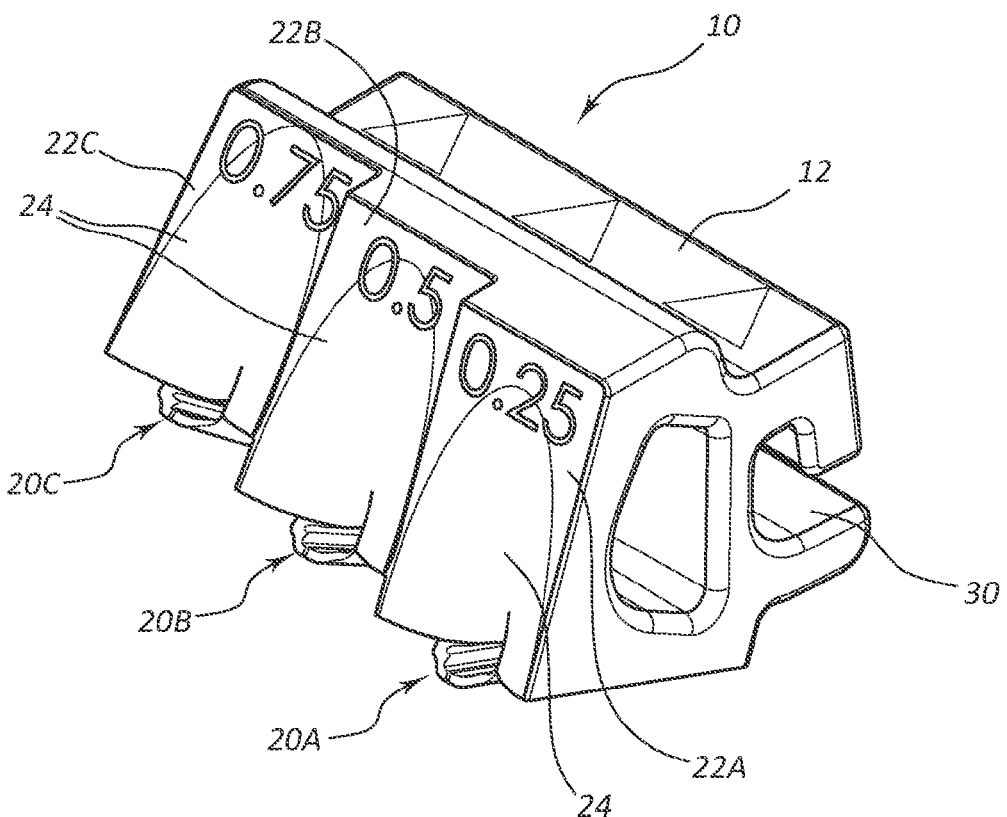
FIGS. 1A-1D are various views of a needle guide assembly according to one embodiment.
Figure 1B:
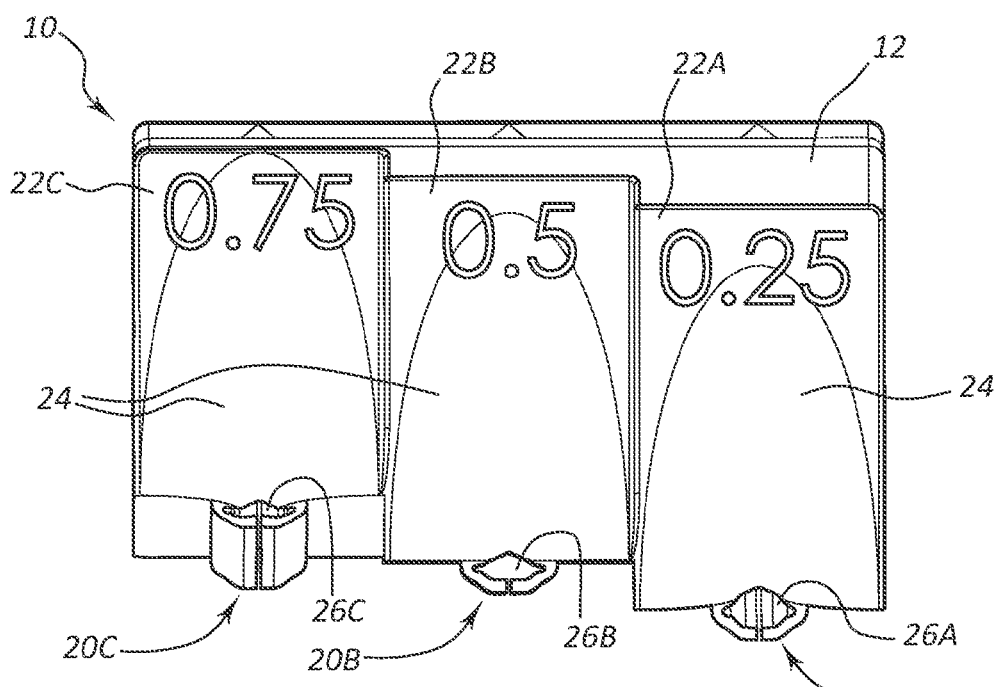
Figure 1C:
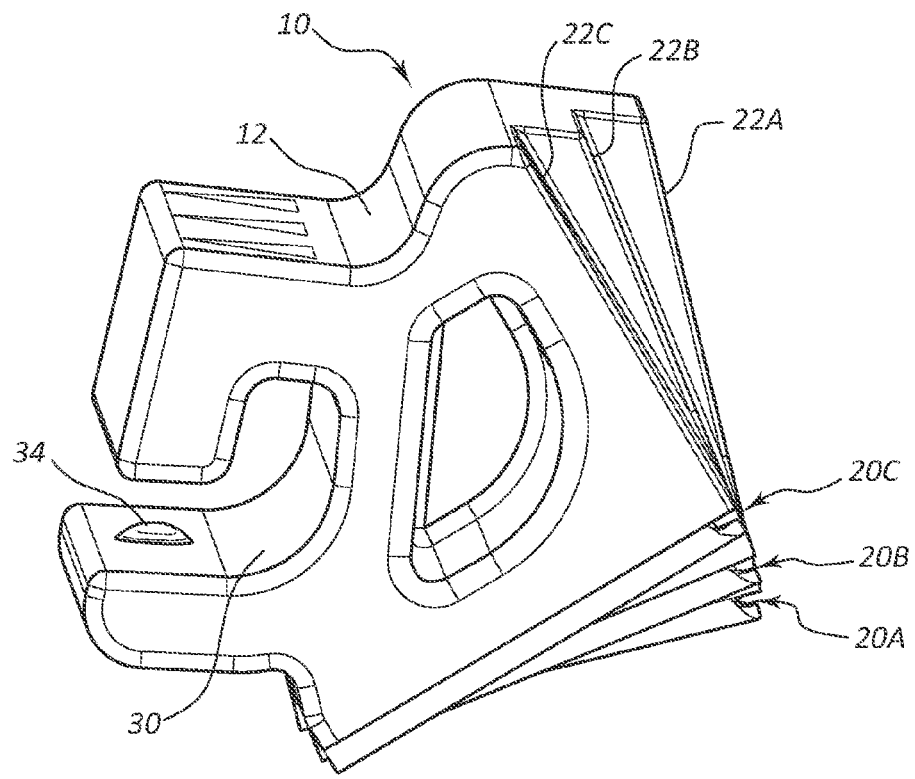

As shown in the perspective shown in FIGS. 1A and 1B, the needle guide body 12 in the present embodiment defines three front faces 22A, 22B, and 22C. At the bottom of each of the front faces 22A-22C, a corresponding guide channel 20A, 20B, and 20C is defined. Each guide channel 20A-20C defines a unique angle of attack, or needle insertion angle, for a needle disposed therein. Correspondingly, each front face 22A-22C is oriented so as to be disposed at substantially a right angle with the longitudinal length of the respective guide channel 20A-20C, as best seen in FIG. 1C. As will be seen further below, the unique angling of each guide channel facilitates proper placement of a needle into a patient so as to access a desired target at a particular subcutaneous depth, such as a vessel, for instance.

Each of the front faces 22A-22C includes a concavely shaped contoured surface 24 that slopes toward an open proximal end 26A, 26B, 26C of the respective guide channel 20A-20C. The contoured surfaces 24 assist in guiding a needle tip placed thereon toward the respective guide channel proximal end opening, thus easing needle insertion into the guide channel. It is appreciated that the front faces can be contoured in other ways as well.

Figure 1D:
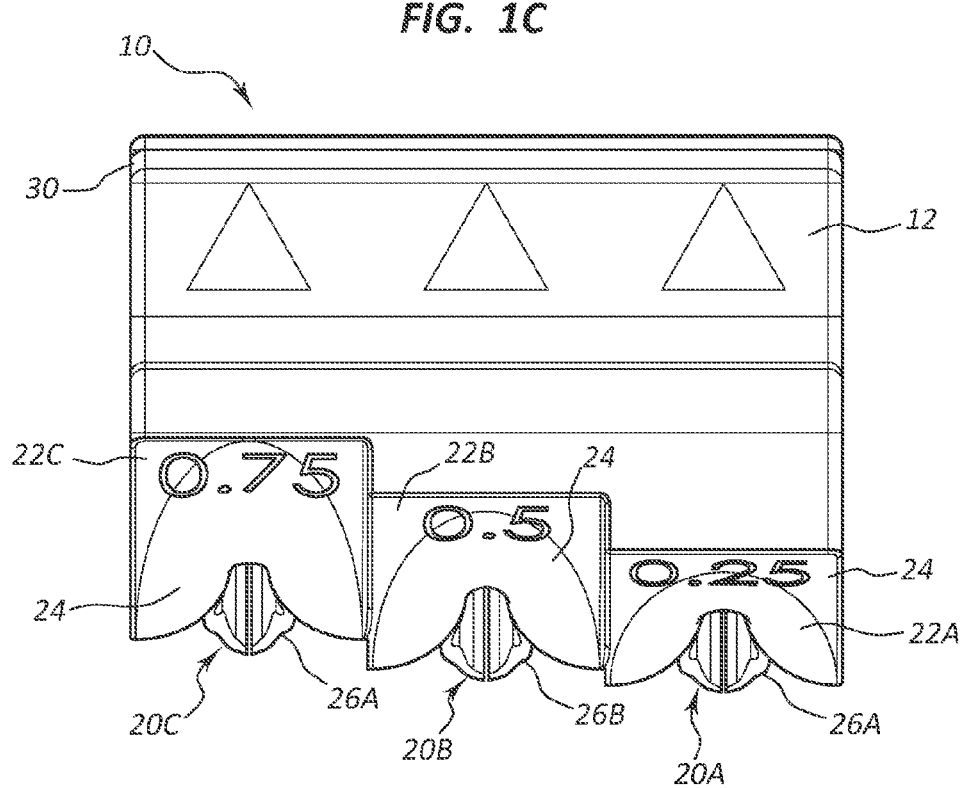

Also, as best seen in FIG. 1D, the proximal ends 26A-26C of the guide channels 20A-20C extend slightly proximal to the respective front faces 22A-22C so as to further ease insertion of the needle tip into the particular guide channel.

The needle guide assembly 10 in the present embodiment is configured so as to be movable with respect to the ultrasound probe or other device with which it is connected. FIGS. 1A and 1C show one implementation of this, wherein the needle guide body 12 includes a track 30 configured to slidably engage a rail 60 (FIGS. 4 and 5) associated with the probe, thus enabling the needle guide body to slide with respect to the probe, as will be further discussed below. As shown, the track 30 includes an L-shaped configuration to assist the needle guide in remaining physically engaged with the rail 60. Note that this is but one example of fixtures to provide connection between the probe and the needle guide; indeed, various other connection schemes can be employed. In addition, it is appreciated that the needle guide can be indirectly or indirectly and temporarily or permanently attached to other surfaces of the ultrasound probe, including side surfaces, end surfaces, etc.

Figure 2:
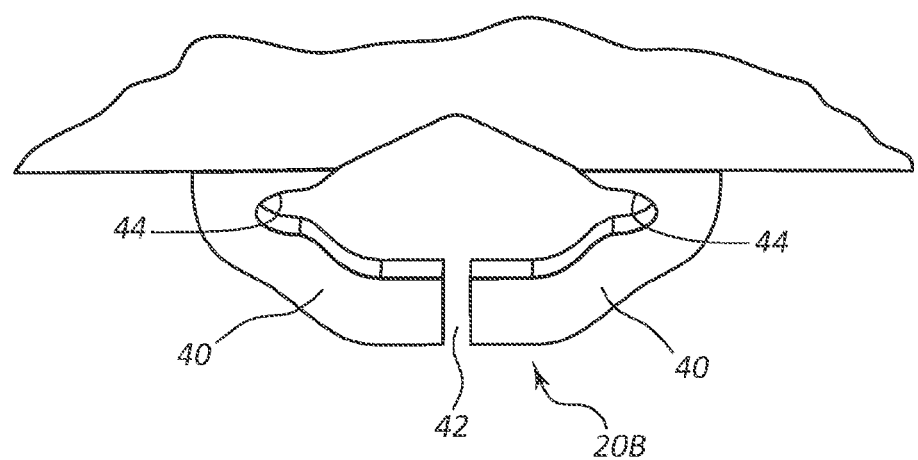
FIG. 2 is an end view of a guide channel of the needle guide assembly of FIGS. 1A-1D.

FIG. 2 shows a proximal end view of the guide channel 20B, which is representative of the other guide channels 20A and 20C, and thus the description here equally applies to each guide channel. As shown, the guide channel 20B includes two arms 40 that each extend distally from the proximal end 26B along the length of the needle guide body 12 to enclose an elongate volume into which a portion of the needle is disposed when the needle is inserted into the guide channel 20B. Cross sectionally, the arms 40 are shaped to extend from the needle guide body 12 and terminate toward each other such that an opening 42 is defined between the terminal arm ends. The opening 42 runs the entire length between the arms 40 so as to define a slot through which a needle or other suitable elongate device can be removed from the guide channel 20A-20C when desired. Notches 44 are also included in each arm 40 proximate attachment of the arm with the main portion of the needle guide body 12. The shape of the arms 40, together with the notches 44, enables the guide channel 20B to expand when needed to receive therewithin needles of a variety of gauges. This in turn offers flexibility for the needle guide 10 and enables it to be used to guide a variety of needles into the patient while still maintaining a suitable amount of directional constraint for the needle such that it enters the patient's body at the intended needle insertion angle. The notches 44 are particularly suited to facilitating expansion of the channel size while maintaining suitable amounts of force imposed on the needle by the arms 40, resulting in the above-mentioned constraint. Note that in one embodiment at least the arms 40 include a thermoplastic or other suitably compliant material to enable bending thereof, as just described.

It is appreciated that the number, size, shape, placement, etc. of the guide channels on the needle guide can vary from what is shown and described herein. Further, though all are similarly configured in the embodiment of FIGS. 1A-1D, it is appreciated that the particular configuration of the guide channels can vary one from another on the same needle guide. Thus, these and other expansions of the principles discussed herein are contemplated.

Figure 3:
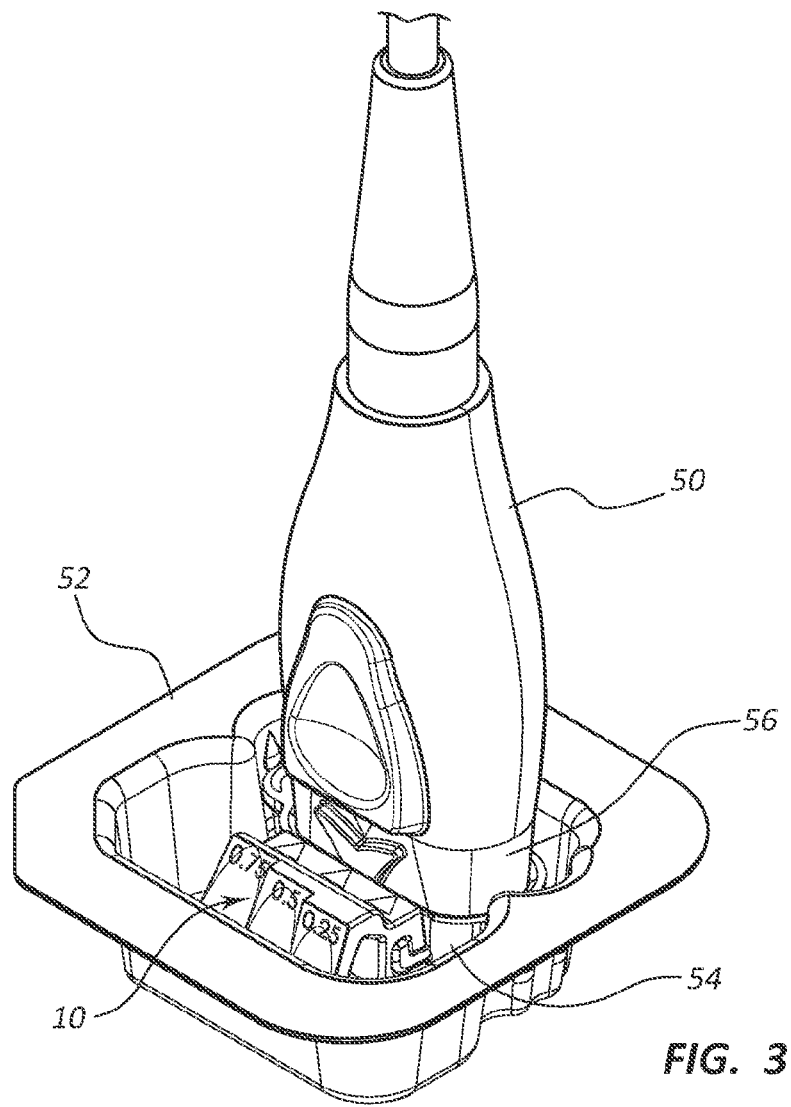
FIG. 3 is a perspective view of a needle guide assembly attached to an ultrasound probe according to one embodiment.

FIG. 3 shows the needle guide assembly 10 disposed in a storage tray 52 together with a probe cap 54. An ultrasound probe 50 is shown with a head thereof removably inserted into the probe cap 54, in preparation for removing the probe cap and the needle guide assembly 10 from the tray 52. As such, it is appreciated that in the present embodiment the tray 52 is an example of a manner in which the needle guide assembly can be packaged, sterilized, and stored prior to use by a clinician, though other packaging configurations are also contemplated.

Figure 4:
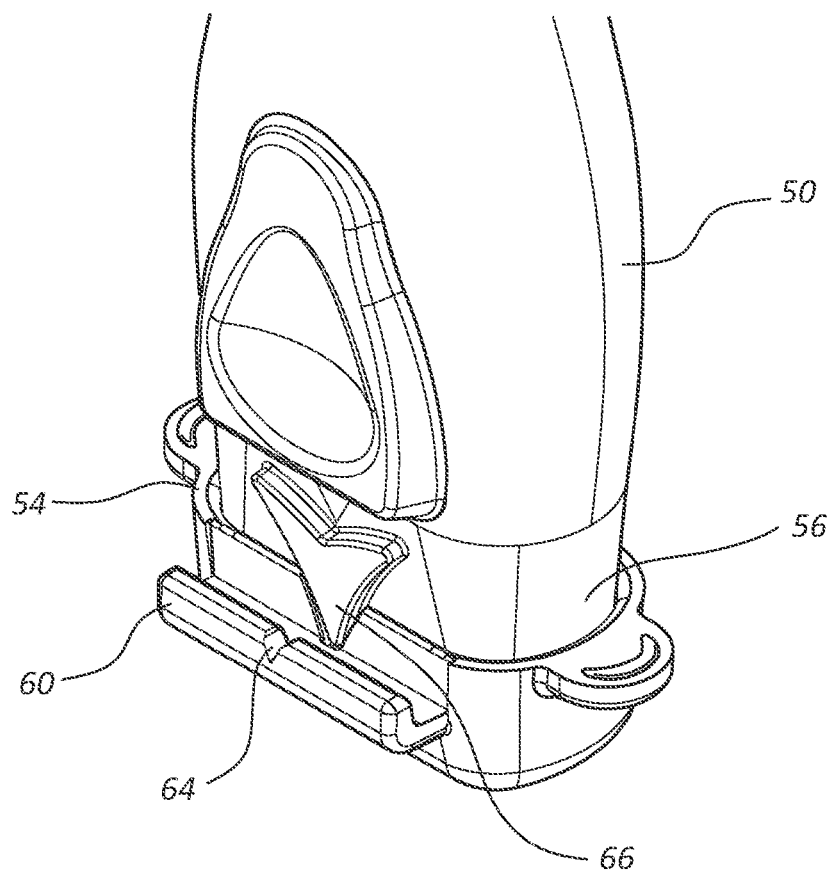
FIG. 4 is a perspective view of a cap attached to an ultrasound probe according to one embodiment.
Figure 5:
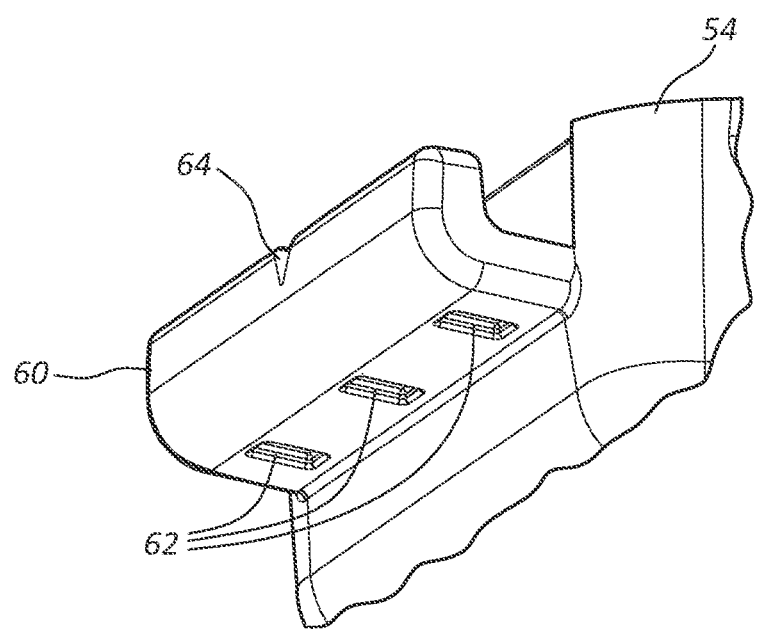
FIG. 5 is a perspective view of a portion of the probe cap of FIG. 4.

FIG. 4 shows the manner of attachment of a head portion 56 of the ultrasound probe 50 with the probe cap 54. FIGS. 4 and 5 show details of the rail 60 that extends from the probe cap 54 and serves as a fixture for attachment of the needle guide assembly 10 thereto. Note that, though a probe cap is used here for attachment, in other embodiments the needle guide assembly can be attached directly to the probe itself, or directly/indirectly to another device. Further details regarding probe caps with which the needle guide assembly described herein can be used can be found in U.S. patent application Ser. No. 13/206,396, filed Aug. 9, 2011, and entitled "Support and Cover Structures for an Ultrasound Probe Head," which is incorporated herein by reference in its entirety.

Figure 6:
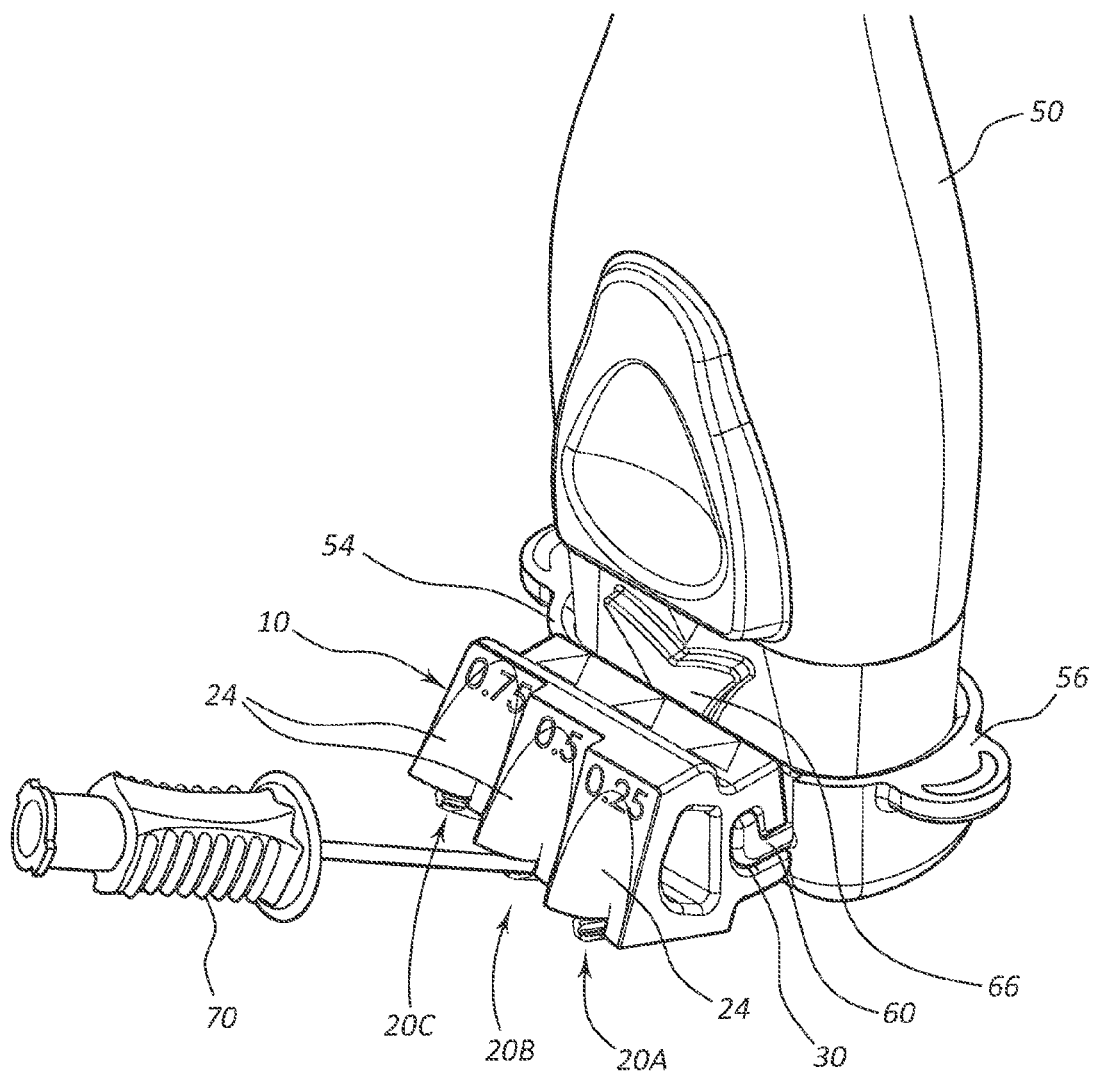
FIG. 6 is a perspective view of the needle guide assembly of FIGS. 1A-1D attached to the probe cap of FIGS. 3 and 4 in a first position.

As shown, the rail 60 includes an L-shaped cross sectional shape to match the shape of the track 30 and to assist in maintaining engagement with the needle guide assembly 10, though it is appreciated that other rail shapes can also be employed. FIG. 6 shows the rail 60 of the probe cap 54 slidably inserted into the track 30 defined by the needle guide assembly 10 such that needle guide assembly is in position for use in guiding a needle into the body of a patient. Note that the probe 50 includes an arrow 66 that indicates the lateral center of the device, for alignment purposes during use. As best seen in FIG. 4, a notch 64 is included on the rail 60 that is aligned with the probe arrow 66 when the probe cap 54 is properly attached the probe 50, and can be used to assist the clinician in aligning a needle with the center of the probe head 56 when no needle guide is used.

FIG. 5 shows that a plurality of detents 62 are included on the rail 60. The detents 62 are spaced so as to individually engage with a nub 34, disposed in the track 30 (FIG. 1C) when a respective one of the guide channels 20A-20C are aligned with the arrow 66 of the probe 50, i.e., in position to guide a needle into the body of the patient.

With the needle guide assembly 10 attached to the probe cap 54 of the probe 50 via the track 30 and rail 60 engagement described above and as shown in FIG. 6, the needle guide assembly can be employed to guide a needle into the body of a patient. As mentioned and as seen in FIG. 6, each guide channel 20A-20C defines a unique needle insertion angle with respect to a longitudinal axis of the probe 50 (or, optionally, the skin surface of the patient when the cap-covered probe head 56 is positioned against the skin in the orientation shown in FIG. 6). The front faces 22A-22C of the needle guide body 12 in FIG. 6 are marked with a depth number indicating the depth at which a needle inserted through the corresponding guide channel 20A-20C would intercept the plane of the image produced by the ultrasound probe.

Thus, in the configuration shown in FIG. 6, the guide channel 20B is aligned with the probe arrow 66 such that a needle 70 that is passed therethrough enters the center of the image produced by the probe 50. As indicated on its front face 22B, the needle insertion angle of the guide channel 20B is such that the needle 70 will intercept the image plane of the probe 50 approximately 0.5 cm below the surface of the skin.

Thus, during an ultrasound imaging procedure, a clinician can observe an image produced by the ultrasound probe of an intended subcutaneous target, such as a vein, when the probe is placed against the skin of the patient. Once the target is imaged by the probe, the clinician can inspect the image and determine or observe the depth of the target under the skin. The clinician can then laterally slide the needle guide body along the probe rail 60 until the guide channel 20A-20C that is marked with a depth corresponding to the depth of the target is aligned with the center of the probe, indicated by the arrow 66 on the probe head 56. Note that the needle guide body 12 is maintained in the selected position via engagement of the nub 34 in the track 30 (FIG. 1C) with the corresponding detent 62 on the rail 60 (FIG. 5). In the configuration shown in FIG. 6, for example, the nub 34 is engaged with the middle detent 62 so as to maintain the guide channel 20B aligned with the center of the probe 50 indicated by the arrow 66. The needle 70 can then be inserted into the selected guide channel 20A-20C (e.g., guide channel 20B in the example shown in FIG. 6) and with continued use of the ultrasound image, the needle can be guided to the intended subcutaneous target.

Figure 7:
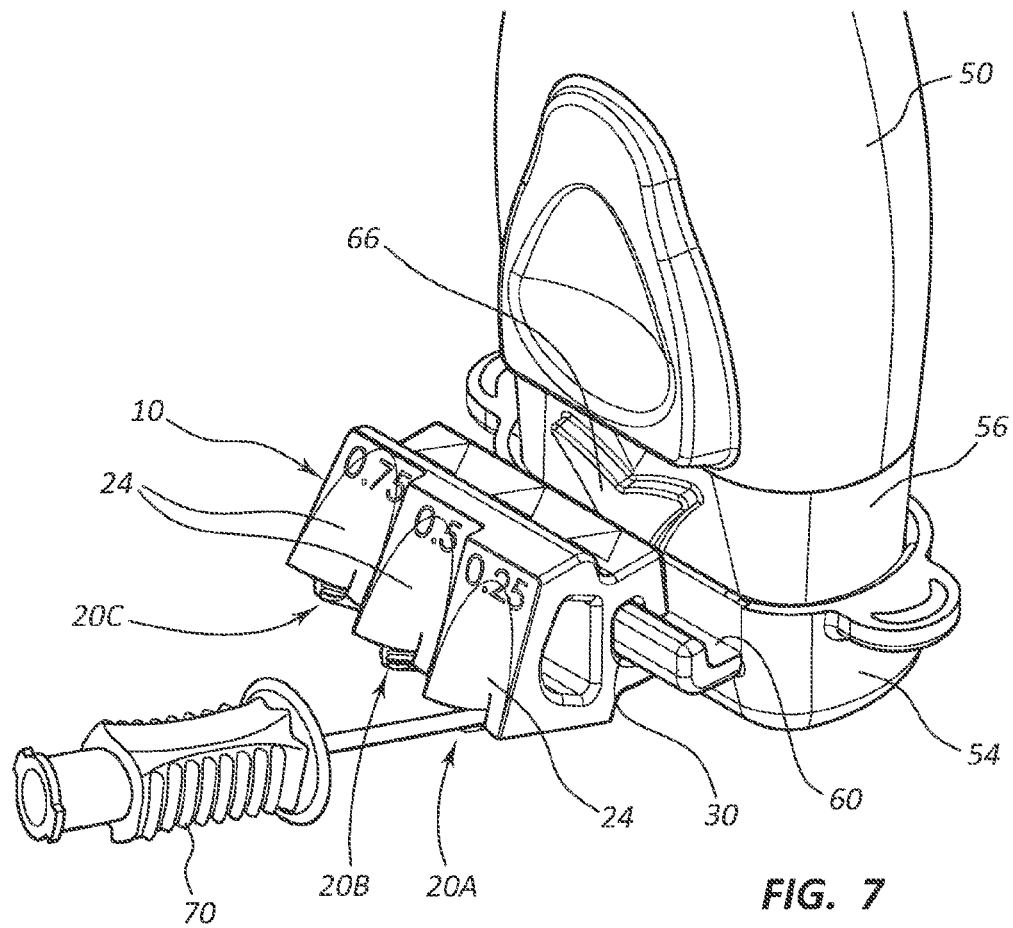
FIG. 7 is a perspective view of the needle guide assembly of FIGS. 1A-1D attached to the probe cap of FIGS. 3 and 4 in a second position.

If a deeper or shallower insertion angle is desired in order to access a deeper or shallower target, respectively, the needle guide assembly 10 can be laterally slid so that the guide channel having the desired target interception depth as marked on the front face 22A-22C is centered with the probe arrow 66. A needle or other suitable elongate instrument can then be inserted through the guide channel and into the patient's skin while the probe 50 is held in place against the skin to continue imaging the target. This is illustrated in FIG. 7, wherein the needle guide assembly 10 is positioned as described and the needle 70 is inserted through the guide channel 20A so as to intercept the ultrasound imager plane at a depth under the skin of approximately 0.25 cm. Note the relatively more shallow needle insertion angle of the guide channel 20A (as evidenced by the less steeply angled needle 70) in FIG. 7 in comparison with the needle insertion angle of the guide channel 20B in FIG. 6.

As described above, each guide channel 20A-20C includes a slot defined by the longitudinal opening 42 between the guide channel arms 40 (FIGS. 1B, 2). Once the target has been accessed, the needle 70 can be removed from engagement with the needle guide assembly 10 by gently pulling the assembly away from the needle such that the needle pulls through the slot of the guide channel 20A-20C and separates from the needle guide assembly.

Figure 8:
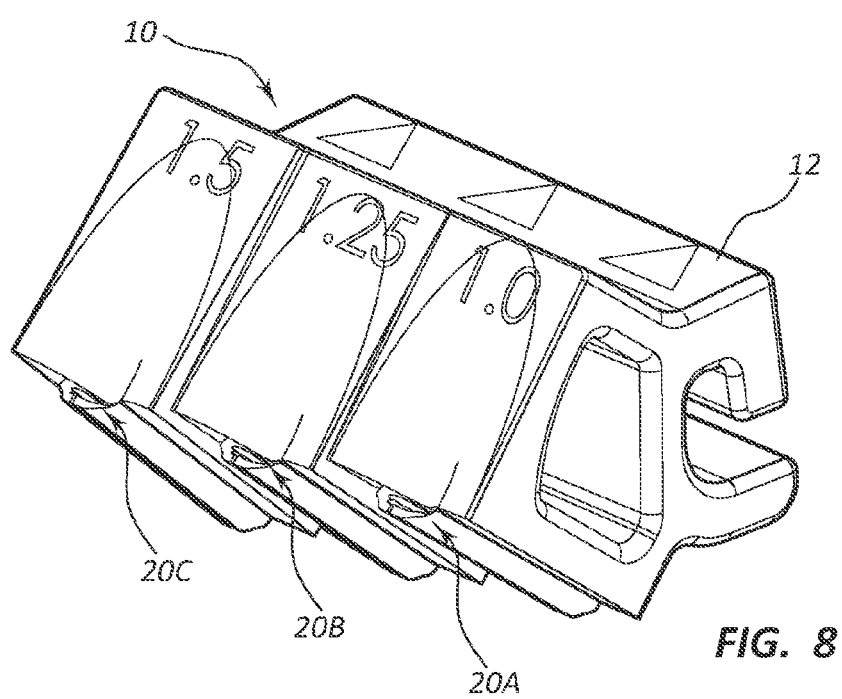
FIG. 8 is a perspective view of a needle guide assembly according to one embodiment.

As was mentioned, the needle guide assembly 10 can include guide channels defining other needle insertion angles and corresponding image plane interception depths. One example of this is shown in FIG. 8, wherein the needle guide assembly body 12 defines needle guide channels 20A, 20B, and 20C that include relatively steeper needle insertion angles than those of the assembly shown in FIGS. 1A-1D, which are useful for accessing relatively deeper subcutaneous targets within the body of the patient. Thus, it is appreciated that guide channels of a variety of needle insertion angles can be included on the needle guide. In addition, the needle guide assembly can define different numbers and positions of guide channels other than what is explicitly shown and described herein. Moreover, the various guide channels and/or front faces corresponding thereto can be color-coded to assist the user in selecting a desired insertion angle. It is also appreciated that, though disclosed herein as being able to accommodate needles of multiple gauges, the guide channels of the needle guide assemblies of other embodiments can be configured for accommodating needles of only a single gauge, if desired. These and other variations to the needle guide assembly are therefore contemplated.

Figure 9A:
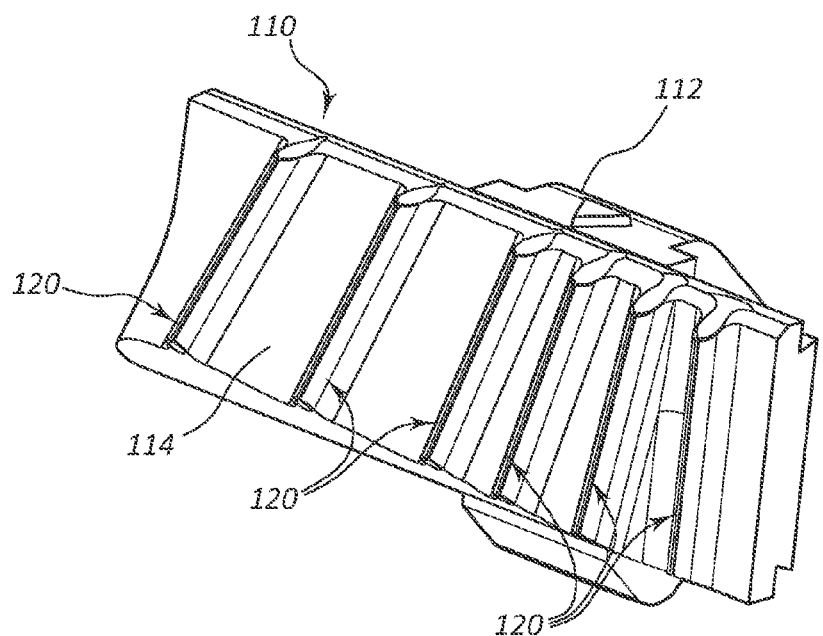
FIGS. 9A-9C are various views of a needle guide assembly according to one embodiment.
Figure 9B:
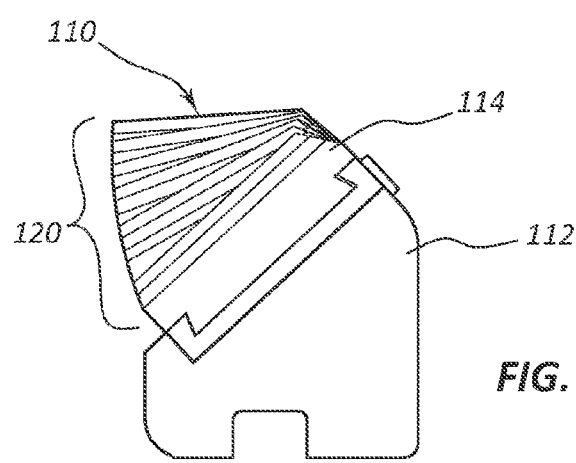
Figure 9C:
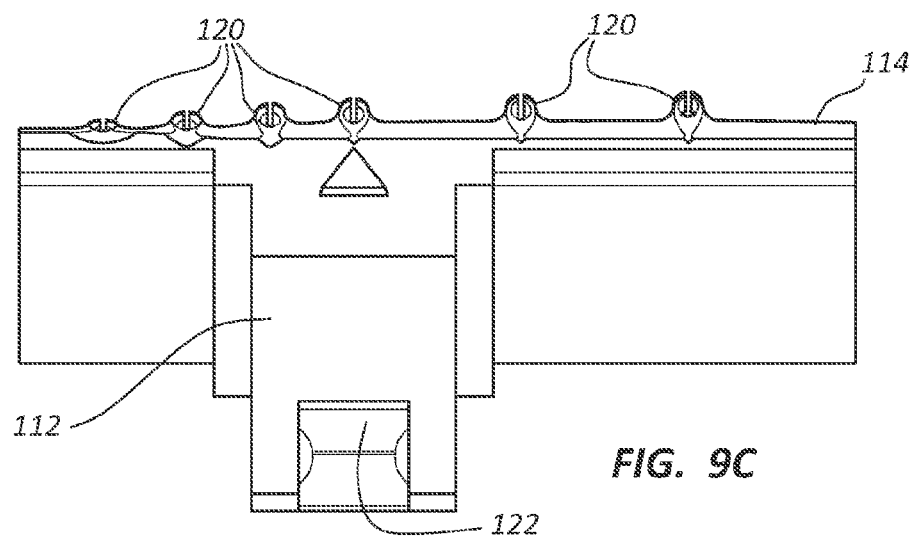

FIGS. 9A-9C depict details of a needle guide assembly 110, according to another embodiment, including a base 112 defining a cavity 122 for attaching the assembly to a corresponding fixture on an ultrasound probe or other suitable device, and a platform 114. The platform 114 includes a plurality of differently angled guide channels 120 and is slidably attached to the base 112 so as to enable the platform to slide laterally with respect to the base.

In greater detail, the platform 114 is shaped such that each guide channel 120 defines a unique needle insertion angle for a needle disposed therein. As with the needle guide assembly of FIGS. 1A-1D, the needle guide assembly 110 is slidably adjustable with respect to the ultrasound probe to enable the clinician to laterally slide the platform 114 of the assembly until the guide channel 120 that matches the required depth to the intended subcutaneous target as imaged by the probe is aligned with the center of the probe. The needle can then be inserted into the selected guide channel 120 and, with continued use of the ultrasound imaging, the needle can be guided to the intended target. Note again that, as with the other embodiments herein, the number, shape, angle, and configuration of the needle guide channels can vary from what is shown and described. Note also that the needle guide assemblies herein can be configured to guide other elongate implements in addition to needles. Further, note that the needle guide assembly can be configured such that the guide channel to be used is positioned at some point other than at the lateral center of the ultrasound probe or other device to which the assembly is operably attached.

FIG. 9B shows the dovetail-type engagement of the platform 114 with the base 112 to enable relative sliding therebetween. Nubs or other interference features can be included on the base 112, the platform 114, or both to enable each guide channel 120 to lock into place when positioned for use. The base 112 can be removable from the ultrasound probe/cap via a snap-fit engagement of the cavity 112 thereof with a suitable fixture on the probe, or permanently affixed thereto. Note that the design of the cavity and fixture can vary from what is shown and described herein, as may be appreciated. In other embodiments the platform can include a semi-circular, parabolic, elliptical, or other non-linear shape to enable the platform to arcuately or otherwise slide about the base. Note that the dovetail-type engagement between the platform and the base can be replaced by other engagement schemes that enable relative movement therebetween.

Figure 10A:
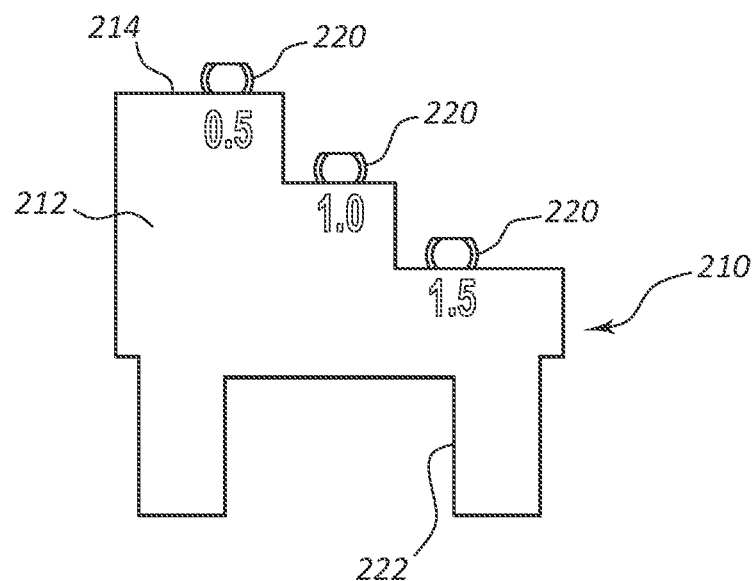
FIGS. 10A and 10B are various views of a needle guide assembly according to one embodiment.
Figure 10B:
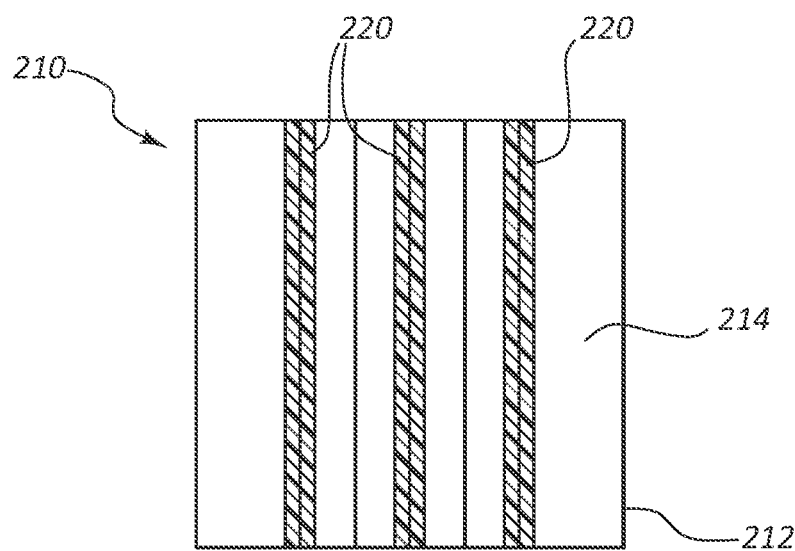

FIGS. 10A and 10B depict another example of a needle guide assembly 210, which includes a base 212 and a stepped platform 214. The platform 214 includes multiple needle guide channels 220 oriented at similar needle insertion angles but at differing distances from a needle insertion point on the skin of the patient when the needle guide assembly 210 is attached to an ultrasound probe. The differing distances of the guide channels 220 from the needle insertion site on the skin (caused by the stepped platform 214) enables each guide channel to guide a needle to a unique depth of intersection with the image plane of the ultrasound probe, and thus to targets at different subcutaneous depths. Thus, a clinician can select a desired one of the needle guide channels 220 that corresponds to the ultrasonically imaged depth of the subcutaneous target. In one embodiment, the clinician slides the ultrasound probe laterally to align the selected needle guide channel 220 with the imaged target as the needle guide assembly is not slidable in the design shown in FIGS. 10A and 10B, though the needle guide can be made movable in other embodiments. Note again that the number and indicated angles of the needle guide assembly 210 as illustrated in the accompanying figures are only examples and other configurations are, of course, possible. In another embodiment, it is appreciated that the guide channels define differing needle insertion angles independent of their separation via the stepped platform. In yet another embodiment, the guide channels are not parallel to one another, but are disposed on the platform so as to converge toward one another.

Figure 11A:
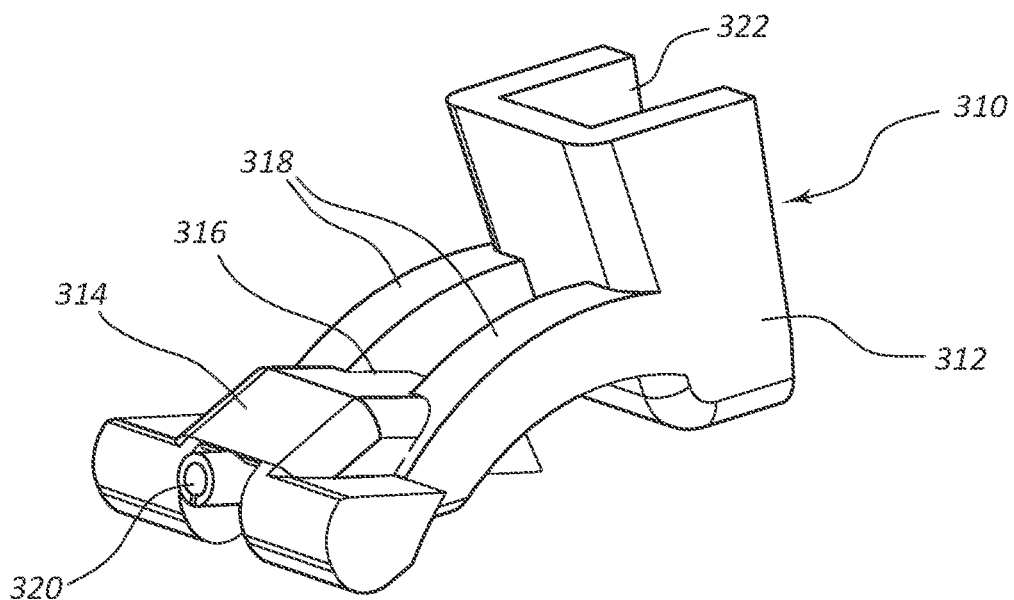
FIGS. 11A and 11B are various views of a needle guide assembly according to one embodiment.
Figure 11B:
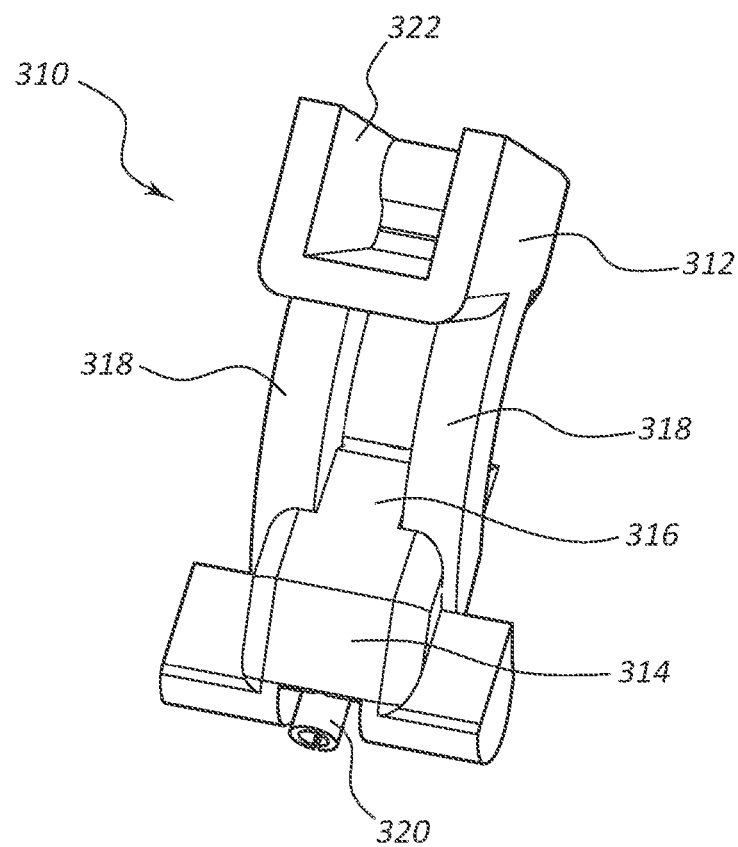

FIGS. 11A and 11B show a needle guide assembly 310 according to another embodiment, including a body 312 defining a cavity 322 for attachment to a probe, probe cap, or the like. A platform 314 including a slotted needle guide channel 320 is also included. In particular, the platform 314 includes a notched arm 316 that is slidably disposed between two arcuate rails 318 of the body 312. So configured, the platform 314 is slidable along the rails 318 to enable the insertion angle of the guide channel 320 to be modified as desired by the user so as to enable a needle inserted therein to intercept an imaged subcutaneous target, such as a vessel.

In one embodiment, the insertion angle with respect to the skin of the patient can vary from about a few degrees to about 90 degrees or more. Note that depth markers can be included on the rails 318 or other portion of the needle guide assembly 310. Note further that in one embodiment the platform can be configured to be releasably lockable to the rails so as to maintain the needle guide channel at a desired angle.

Figure 12A:
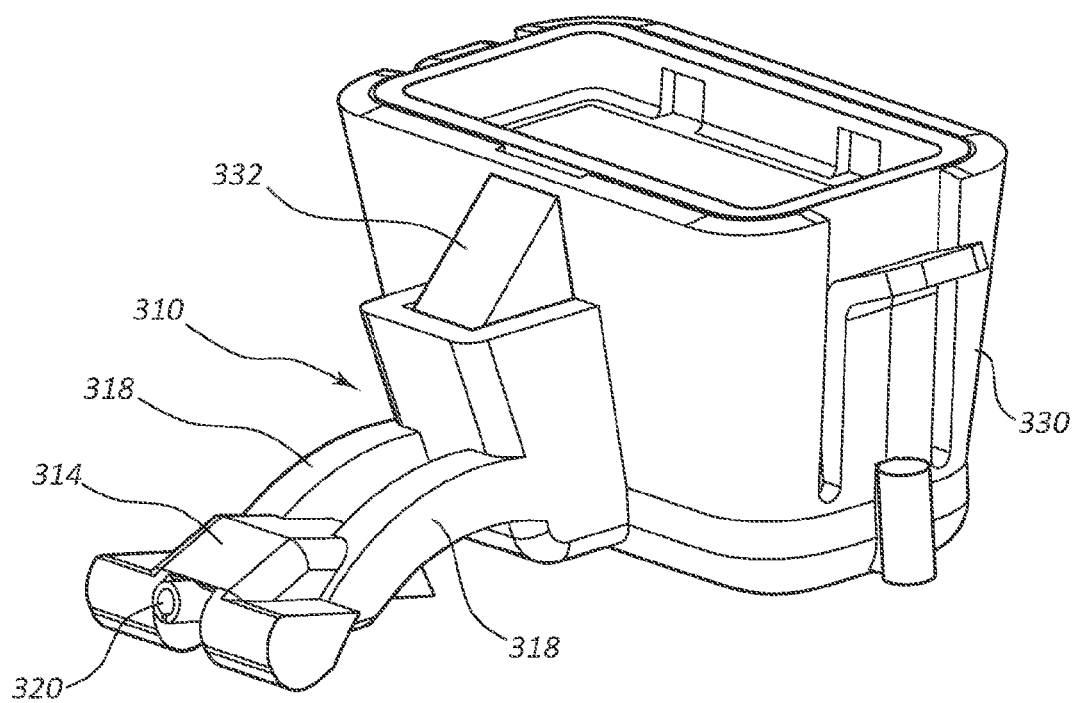
FIGS. 12A and 12B are various views of the needle guide assembly of FIGS. 11A and 11B attached to a probe cap for an ultrasound probe according to one embodiment.
Figure 12B:
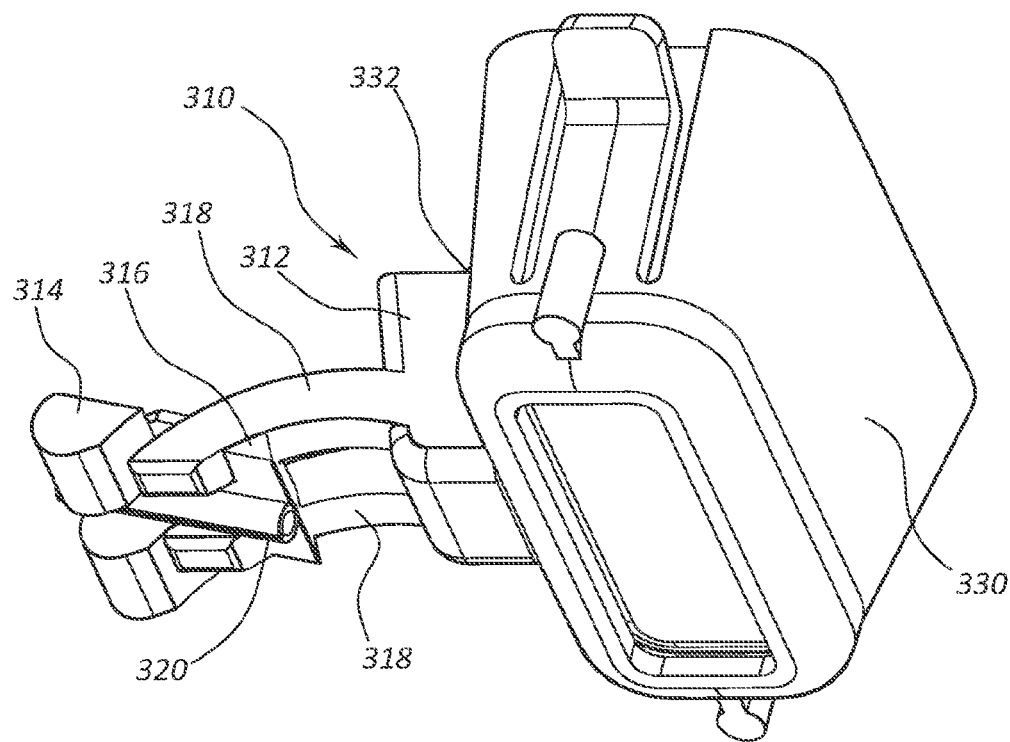

FIGS. 12A and 12B show the manner of releasable engagement of the needle guide assembly 310 with a fixture 332 of a probe cap 330, according to one possible mounting scheme. Of course, other direct or indirect engagement schemes of the probe/probe cap with this or the other needle guide assemblies disclosed herein can be employed.

FIGS. 13A-33B depict additional examples of needle guide assemblies, including guide channel structures for accommodating differently sized needles and needle stop features for preventing unintended distal advancement of the needle after insertion into the needle channel.

Figure 13A:
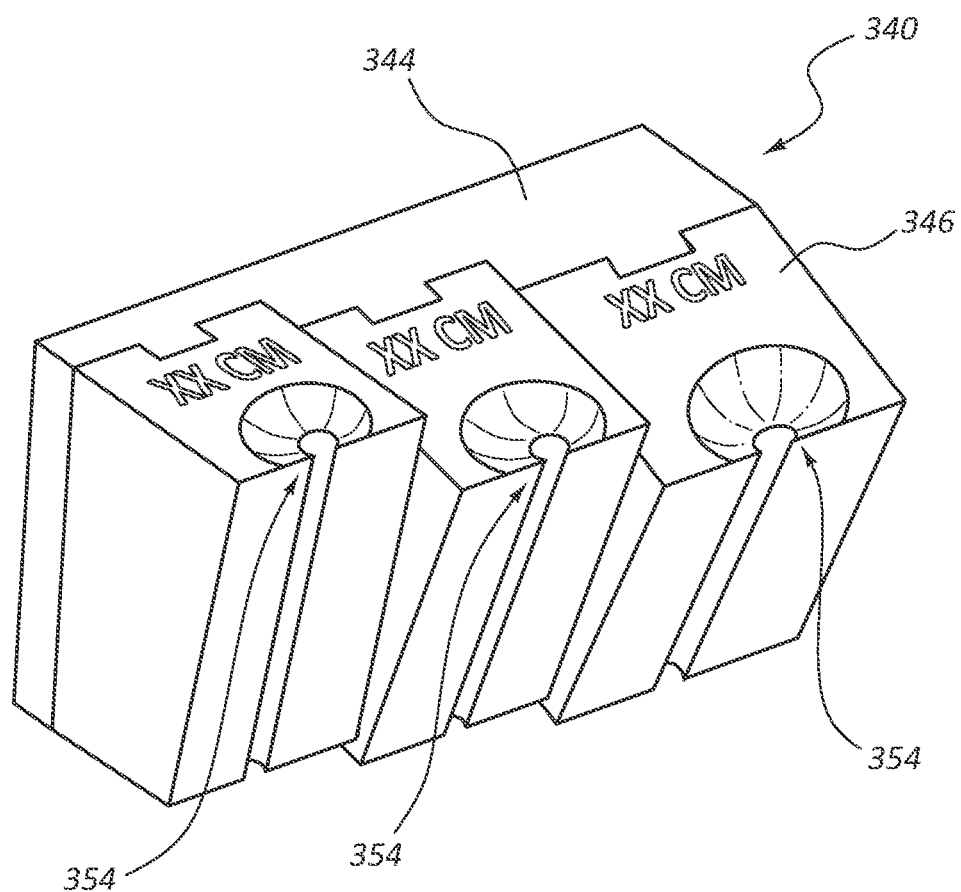
FIGS. 13A-13C show various views of a needle guide assembly in accordance with one embodiment.
Figure 13B:
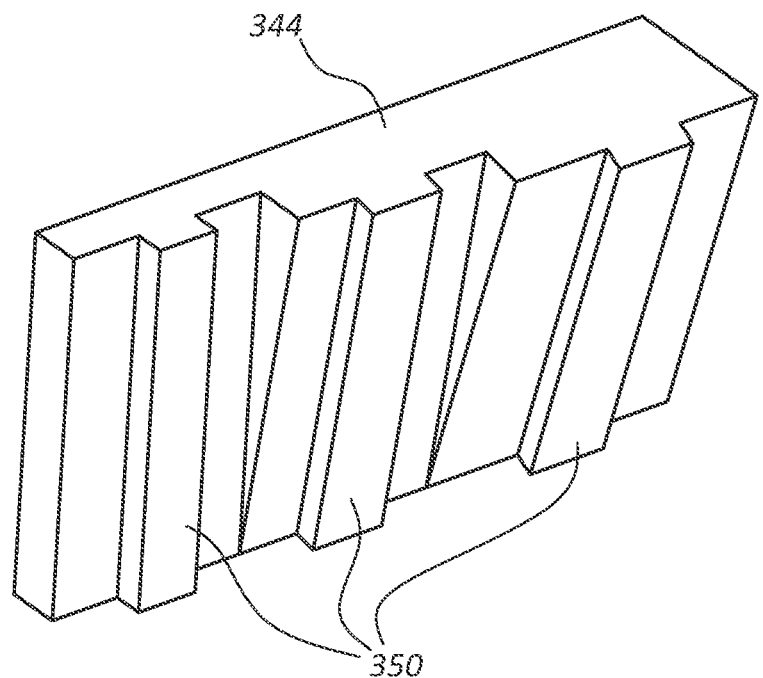
Figure 13C:
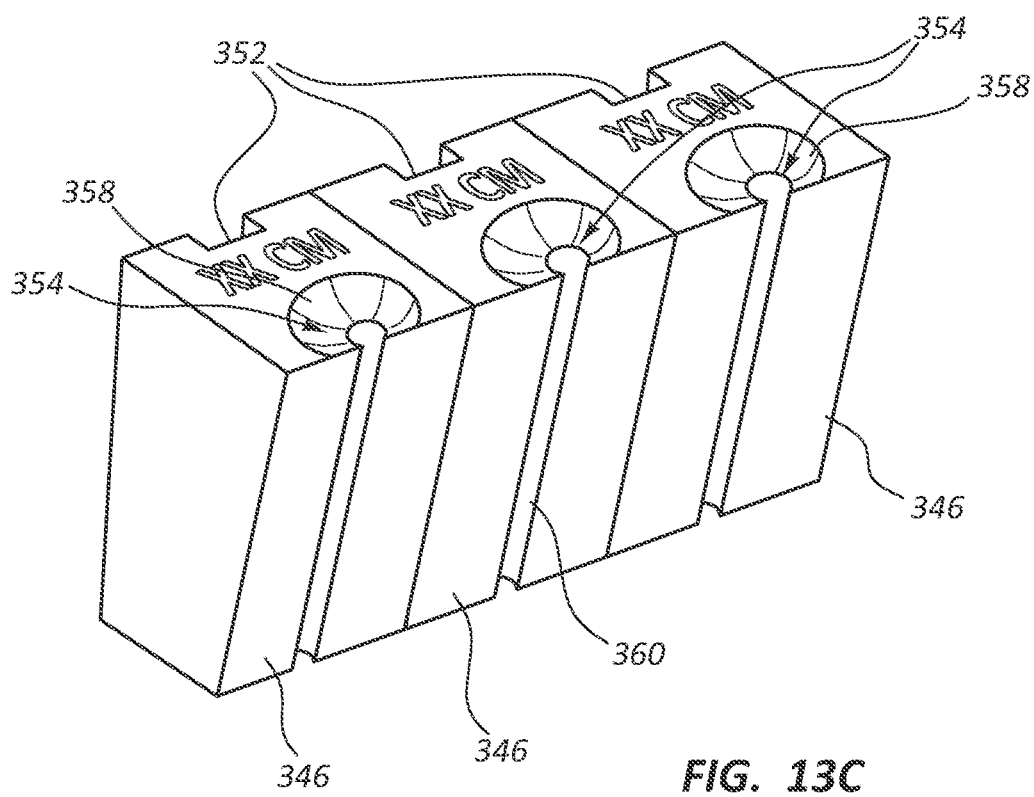

FIGS. 13A-13C depict one example of a needle guide assembly, generally designated at 340, according to one embodiment. As with previous embodiments, the needle guide assembly 340 is configured for attachment to a handheld probe of an ultrasound imaging device, a cap attachable to the probe, or other suitable component. For instance, an attachment interface can be included that enables the needle guide assembly to be slidably and removably attached to an ultrasound probe.

In greater detail, the needle guide assembly 340 includes a base 344 and a plurality of blocks 346. As shown in FIG. 13B, in the present embodiment the base 344 defines a plurality of linear rails 350 that are set at differing angles with respect to one another. Correspondingly, FIG. 13C shows a set of three blocks 346, wherein each block includes a guide channel 354 sized to receive therethrough a needle such that the channel can guide a needle during needle insertion procedures.

Each block 346 further defines a track 352 sized to inter-engage with a corresponding one of the rails 350 of the base 344 so as to enable attachment of each block to the base. Note that in the configuration shown in FIGS. 13A-13C, the blocks 356 are identically sized and configured, though in other embodiments each block may differ from other blocks. Note further that, though including three rails for receiving thereon three blocks, the base of the needle guide can define more or fewer than three rails so that any suitable number of blocks can be included thereon.

As depicted in FIG. 13A, each block 346 can be joined to the base 344 by receiving the rail 350 into the track 352 of the corresponding block. This engagement can be secured via ultrasonic or other welding, adhesive, friction fit, dovetail or other corresponding rail/track inter-engagement configurations, etc. In yet other embodiments, other modes of attachment of the blocks to the base can be employed, including adhesive, ultrasonic welding, mechanical fasteners, etc. Because each rail 350 is differently angled, the blocks 346 attached thereto are also differently angled with respect to one another. This in turn causes the guide channel 354 of each block 346 to define a unique angle of attack with respect to the channels of the other blocks. So configured, the needle guide assembly 340 includes a plurality of guide channels 354 that each define one of a plurality of needle insertion angles with respect to the skin of a patient during a procedure to introduce the needle into the patient. Note that each needle guide channel 354 further defines a slot, or slit 360 longitudinally defined along the guide channel to enable the needle to be removed therefrom when desired.

The needle guide assembly configuration shown in FIGS. 13A-13C enables the blocks containing the guide channels to be identically mass produced, thus providing a modular solution for the blocks. This in turn increases manufacturing efficiency and allows for ready customization of the base or blocks if needed. In one instance, the blocks can be manufactured in different colors, then assembled together on the base such that each color indicates a different angle of attack for the respective needle channel. In another embodiment the color coding can indicate different needle sizes that can be accommodated by the guide channel of each respective block. In one embodiment, the angles of attack for the needle channels with respect to the patient's skin can vary from about 15 degrees to about 45 degrees (so as to enable needle interception with vessels of different subcutaneous depths), with each needle channel varying in angle of attack from the other channels by about 2-5 degrees, though many other angles and angle of attack ranges can be employed.

Note that the attachment interface mentioned above can be permanently or removably attached to the base 344 of the needle guide assembly 340. Indeed, in one embodiment the base 344 is slidably attached to the attachment interface so that a desired one of the blocks 346 can be laterally slid into alignment with a central portion of the ultrasound probe to which the needle guide is attached. Thus, during an ultrasound imaging procedure a clinician can observe an image produced by the ultrasound probe of an intended subcutaneous target, such as a vein, when the probe is placed against the skin of the patient. Once the target is imaged by the probe, the clinician can observe and/or determine the depth of the target under the skin and the angle of attack required for the needle to intercept the subcutaneous target. With the needle guide assembly 340 attached to the side or other suitable surface of the ultrasound probe, the clinician can laterally slide the base 344 of the assembly until the block 346 including the guide channel 354 that matches the required angle of attack for the needle is aligned with the center of the probe. The needle can then be inserted into the selected channel 354 and with continued use of the ultrasound image, the needle can be guided to the intended subcutaneous target. Note that the number, shape, angle, and configuration of the needle guide channels can vary from what is shown and described herein. Note also that the needle guide assembly can be configured to guide other elongate implements in addition to needles. In addition, in one embodiment each block of the needle guide assembly is color-coded to indicate needle channels including a particular angle of attack. Other similar variations to the needle guide assembly are also contemplated.

In one embodiment, the needle guide assembly shown in FIGS. 13A-13C is configured to attach to a cap removably attached to a head portion of an ultrasound probe. Further details regarding such an ultrasound probe cap may be found above and in U.S. Patent Application Publication No. 2011/0087107, filed Oct. 8, 2010, and entitled "Spacers for Use with an Ultrasound Probe." Further details regarding certain aspects of some of the needle guides discussed herein may be found in U.S. Pat. No. 5,235,987, entitled "Needle Guide." Each of the aforementioned documents is incorporated herein by reference in its entirety.

In another embodiment it is appreciated that the needle guide blocks can be varied in shape, design, and/or angle of attack. For example, the angle of attack of the guide channel of each block can vary such that when the clocks are arranged together on a base or other platform, each block defines a unique angle of attack. In such a case, the base can be uniform in shape as opposed to the base 344 shown in FIG. 13B.

Figure 14A:
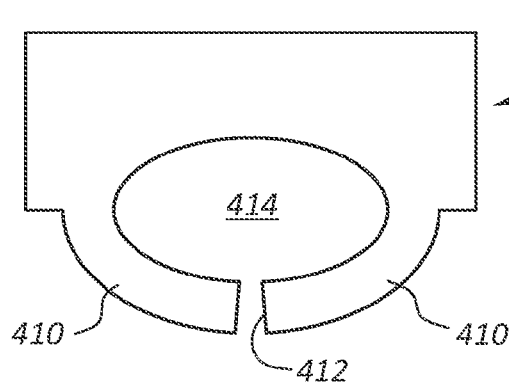
FIGS. 14A and 14B are various views of a guide channel of a needle guide assembly in accordance with one embodiment.

FIGS. 14A-17B depict various structural examples of a guide channel 400 that can be included with a needle guide, such as those needle guides described above or with other needle guides not explicitly shown and described herein. In particular, the guide channel structures discussed here are capable of receiving therein needles of multiple gauges/sizes, thus expanding the flexibility and use of the needle guide. For instance, FIGS. 14A and 14B show the guide channel 400 as including two compliant, arcuate arms 410 that define an oval volume or channel area 414 in which the cannula of a needle can be disposed during use of the needle guide in guiding the needle into the patient's body. The arms 410 extend from the body of the needle channel structure 640 and converge toward one another to define a small slit 412 therebetween and to define the channel area 414, as described. So configured, the arms 410 are able to expand to receive therewithin a cannula of a needle of one of a range of needle gauges.

Note that the needle in one embodiment is introduced into the guide channel 400 via a proximal end thereof. Once the needle is placed within the guide channel 400, the compliance of the arms 410 enables a sufficient but not excessive amount of friction force to be imposed on the outer surface of the needle cannula by the arms, thus assisting with retention of the needle within the channel regardless of needle size (provided the needle size is within an acceptable predetermined range of sizes). At the same time, however, the friction force is small enough to enable relative ease of longitudinal sliding of the needle through the guide channel 400, such as when the needle is advanced or retracted, again regardless of needle size. The needle can be readily removed from the needle channel 640 via the slit 412 defined between the ends of the arms 410.

Figure 15A:
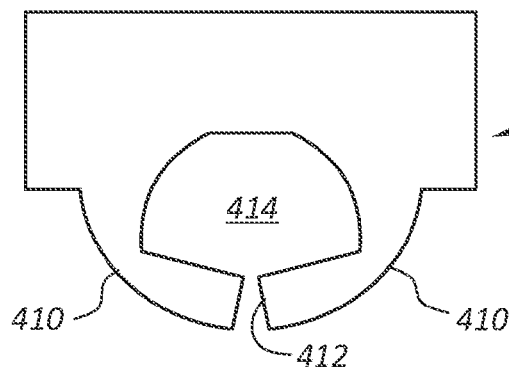
FIGS. 15A and 15B are various views of a guide channel of a needle guide assembly in accordance with one embodiment.
Figure 15B:
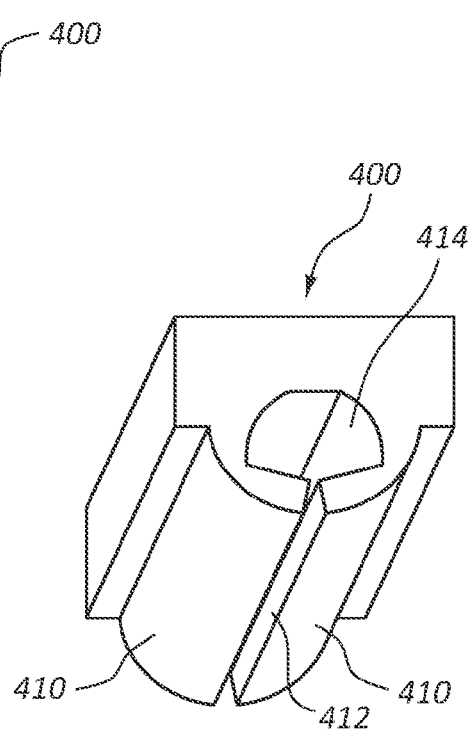

FIGS. 15A and 15B show that in one embodiment, an inner surface 418 of the arms 410 of the guide channel 400 defines three contact surfaces 420 that are positioned so as to contact a needle received therein, regardless of the gauge of the needle within a predetermined gauge range. Thus, the use of the contact points enables the needle cannula to be secured within the channel while still enabling longitudinal sliding thereof without undue resistance. Note that more or fewer contact points can be included in the guide channel design. Examples of possible needle gauge sizes the guide channel in this and other embodiments can receive include 18-30 ga., though other gauge sizes and ranges are also possible. Moreover, the needle guides and guide channels can be employed for differing procedures, such as peripheral IV's, general and blood collection needles, biopsy needles, etc.

Figure 16A:
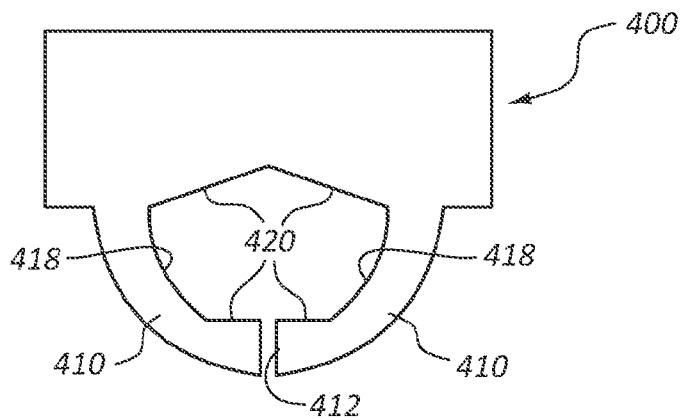
FIGS. 16A and 16B are various views of a guide channel of a needle guide assembly according to one embodiment.
Figure 16B:
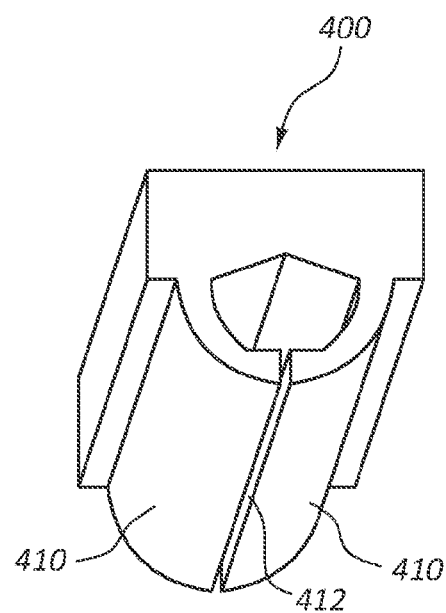
Figure 17A:
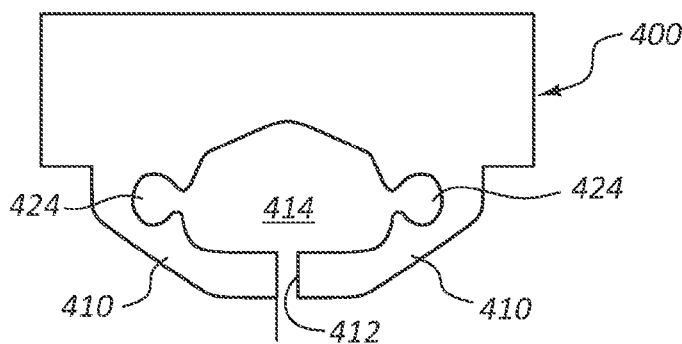
FIGS. 17A and 17B are various views of a guide channel structure of a needle guide assembly according to one embodiment.
Figure 17B:
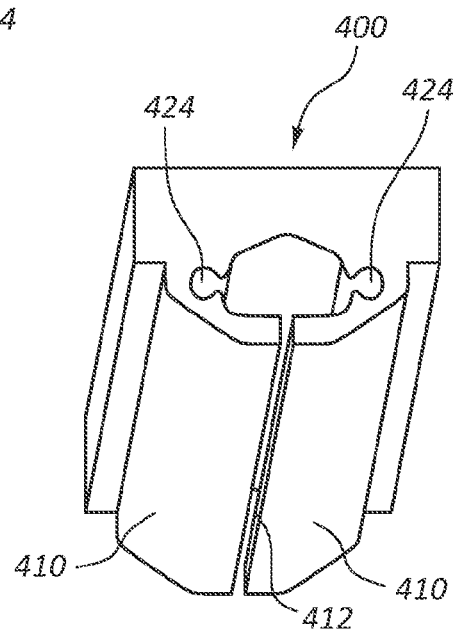
Figure 18A:
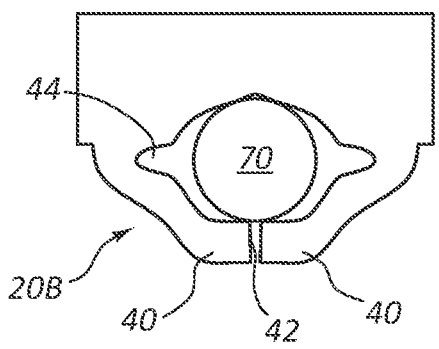
FIGS. 18A-20B show use of the guide channel structure of FIG. 2 with differently-sized needles.
Figure 18B:
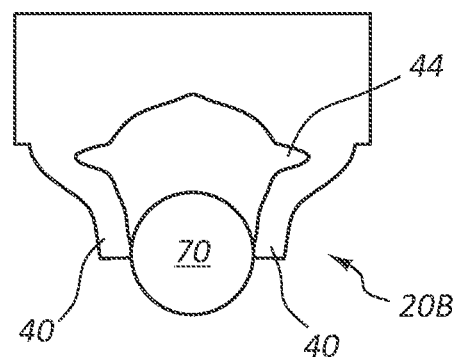
Figure 19A:
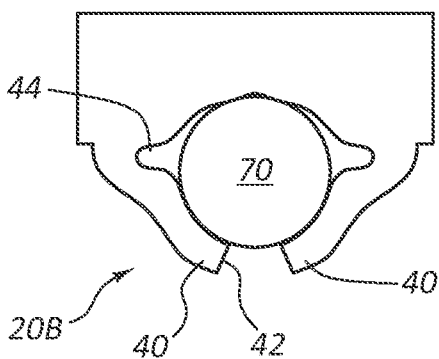
Figure 19B:
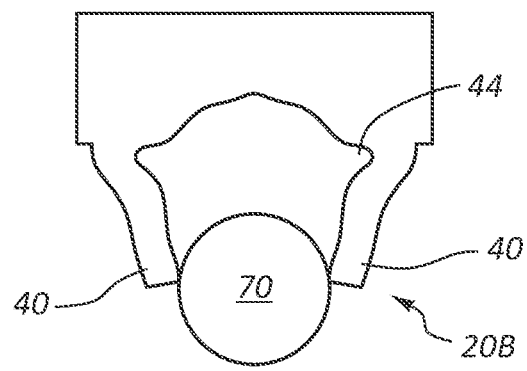
Figure 20A:
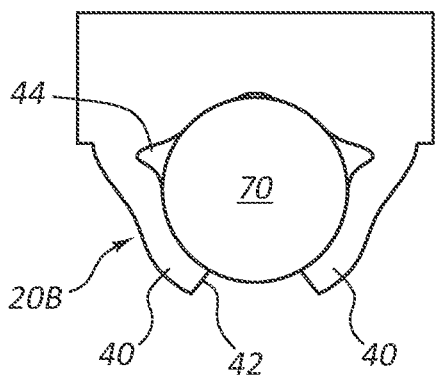
Figure 20B:
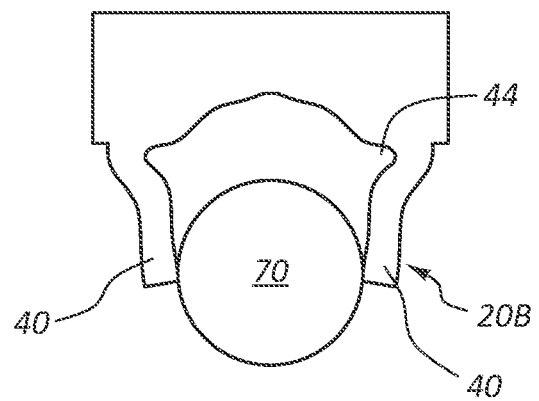

FIGS. 16A and 16B show another embodiment of the guide channel 400, wherein the inner arm surface 418 bounds the channel area 414 and defines the plurality of needle contact surfaces 420. FIGS. 17A and 17B show the guide channel 400 with the channel area 414 configured similarly to that of FIGS. 16A and 16B, but further including opposing notches 424 defined by each arm 410.

The arms 410 including the notches 424 of FIGS. 17A and 17B function similarly to the arms 40 and notches 44 shown in the guide channel 20B discussed in connection with FIG. 2, above, in accommodating differently sized needles disposed within the channel. In that embodiment and as seen in FIGS. 18A-20B, the notches 44 enable the arms 20B to widen a sufficient amount to accommodate differently-sized needles 70 while still providing a suitable amount of force thereon so as to stabilize the needle during advancement through the guide channel needle guide use. Note that the number, shape, and other details of the notches can vary from what is shown and described here. In addition, the particular size and shape of the arms can also vary. Moreover, the needle channel structures disclosed herein can be employed to receive and support other devices, such as IV or other catheters, for instance.

Figure 21:
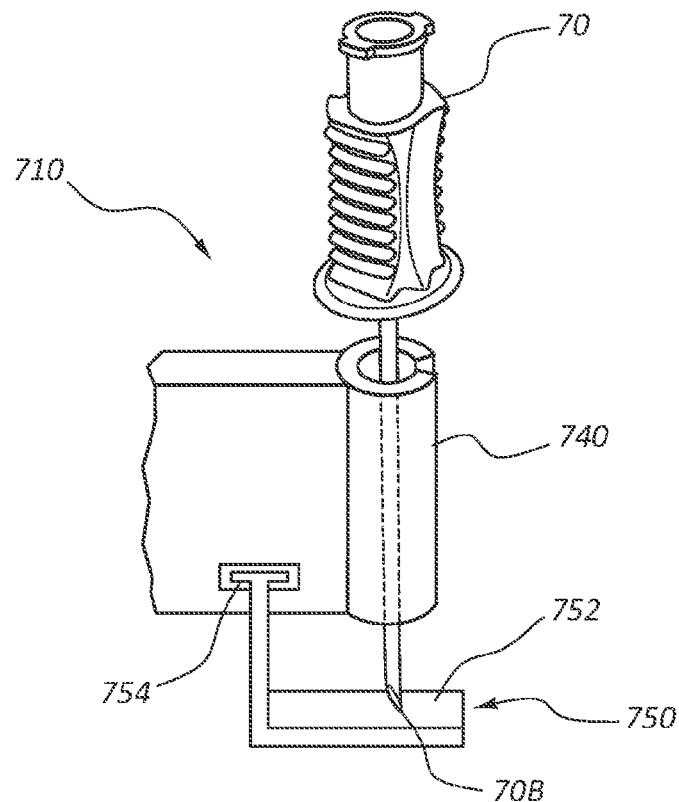
FIG. 21 is a view of a needle guide assembly including a needle stop feature according to one embodiment.

Reference is now made to FIG. 21 in describing various features of a needle guide assembly, including a needle stop feature for retaining a needle disposed in the guide channel of the needle guide assembly, such as the needle guide assemblies discussed herein. Retention of the needle in a set position prior to advancement into the patient enables the ultrasound probe or other device to which the needle guide is attached to be suitably positioned while keeping the distal end of the needle a safe distance away from the patient's skin, thus preventing inadvertent scratching of the patient or other undesired contact with the needle. The needle stop features to be described herein therefore prevent needle advancement without some input or force supplied by the user thereof.

FIG. 21 depicts one embodiment of a needle guide assembly 710, including a guide channel 740 for receiving therein the needle 70. In accordance with present embodiments, a needle stop feature 750 is included and embodied here as a lock arm 752 that is attached to a portion of the needle guide assembly 710 at an attachment point 754 and is disposed proximate the distal end of the guide channel 740.

The lock arm 752 is positioned so as to prevent further distal movement of the needle 70 after insertion thereof into the guide channel 740. In one common instance, this enables the ultrasound probe to which the needle guide assembly 710 is attached to be positioned as desired by the clinician against the patient's skin while the sharp distal tip 70B of the needle 70 is supported by the lock arm 752. This prevents inadvertent advancement of the needle and undesired contact of the needle distal tip with the patient's skin or other surface. When advancement of the needle is desired, the lock arm 752 can be moved out of the distal advancement path of the needle 70 via removal of the arm from the needle guide assembly 710, bending or other deformation thereof, etc. Advancement of the needle 70 as desired can then proceed. Note that the lock arm shown here is but one example; indeed, the lock arm can include many shapes, sizes, configurations, etc. Also, the lock arm can be permanently or removably attached to the needle guide assembly, ultrasound probe, or other suitable component.

Figure 22:
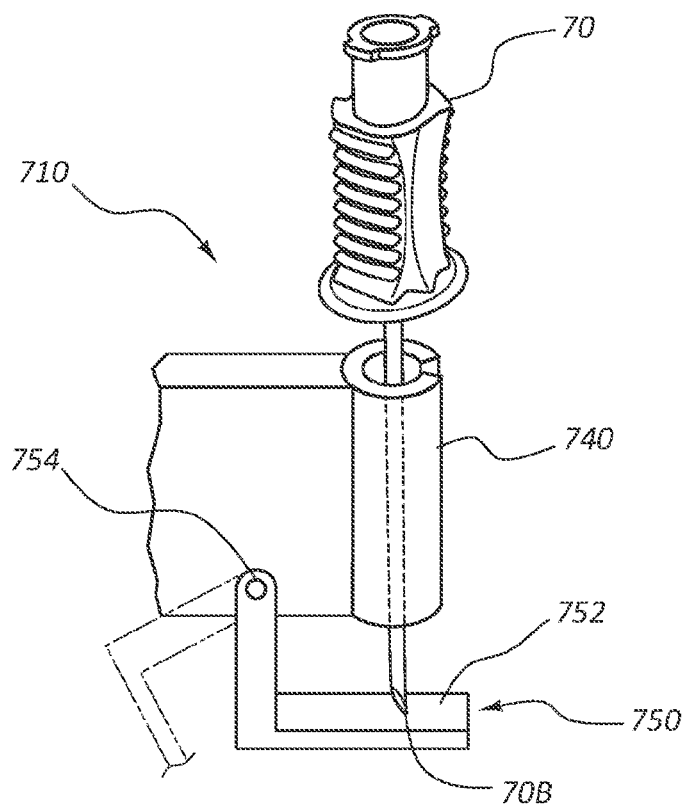
FIG. 22 is a view of a needle stop feature according to one embodiment.

FIG. 22 shows one variation of the lock arm 752, wherein the arm is pivotally attached to the needle guide assembly 710 so that that arm can be swiveled out of the advancement path of the needle 70 when distal needle advancement is desired. These and other variations to the lock arm are therefore contemplated.

Figure 23:
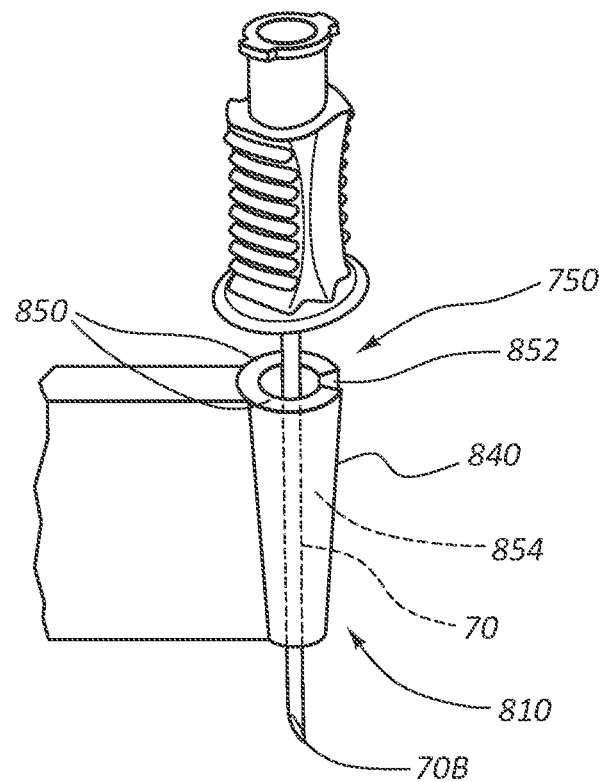
FIG. 23 is a view of a needle stop feature according to one embodiment.

FIG. 23 gives another example of a needle guide assembly 810 including a guide channel 840 defined by two arcuately extending arms 850 that meet to define a longitudinally extending slit 852. The needle lock feature 750 for preventing inadvertent contact or advancement of the needle 70 is also included, wherein the guide channel 840 for passage therethrough of the needle 70 is shaped so that a channel volume 854 defined by the guide channel is distally tapered. The distal taper of the channel volume 854 provides a suitable amount of resistance to distal advancement of the needle 70, thus preventing distal advancement of the needle 70 without the application of user force thereto. Note that this embodiment enables the distal tip 70B of the needle 70 to be positioned as desired by the clinician, which tip will remain in place until moved again by the clinician.

Figure 24:
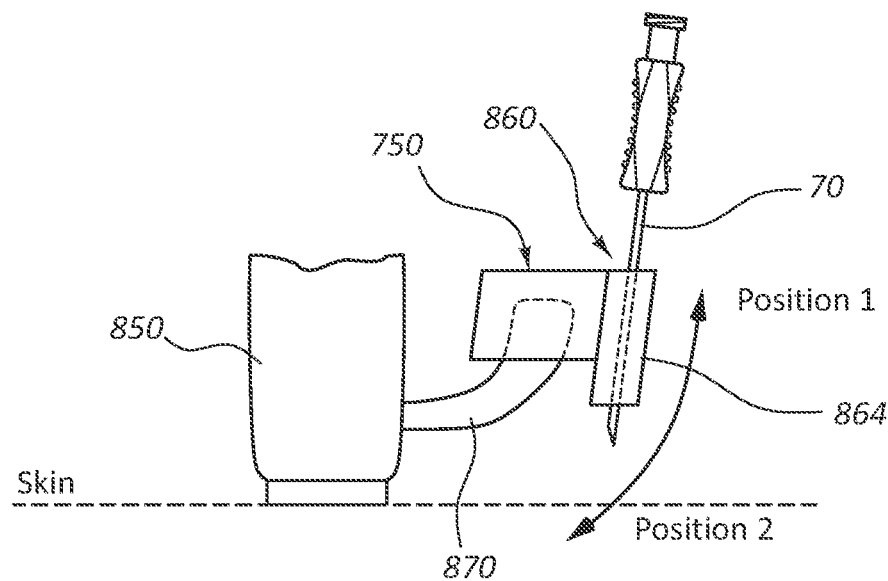
FIG. 24 is a view of a needle stop feature according to one embodiment.

FIG. 24 gives another example of a needle guide assembly 860 including a guide channel 864 and needle lock feature 750 for preventing inadvertent contact or advancement of the needle 70, wherein the needle guide assembly itself is pivotally attached to an ultrasound probe 850 via an arm 870 pivotally attached to the probe. This enables the needle 70 received by the guide channel 864 to be positioned in one of at least two positions: a first position wherein the needle 70 is disposed relatively far from the patient's skin, and a second position (caused by distal pivoting of the needle guide assembly arm 870) wherein the distal tip of the needle is positioned relatively close to the skin surface. The clinician can then distally advance the needle 70 as desired. The pivoting arm 870 can include one or more locking features for locking the needle guide in the first and/or second positions. Moreover, additional positions can be included.

Figure 14B:
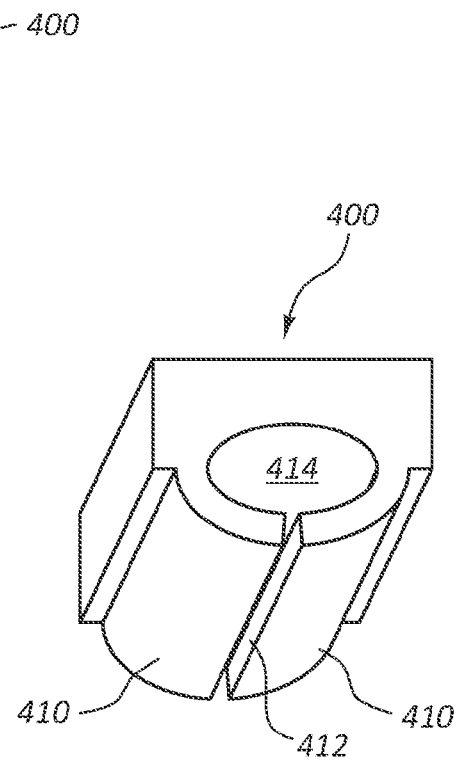
Figure 25A:
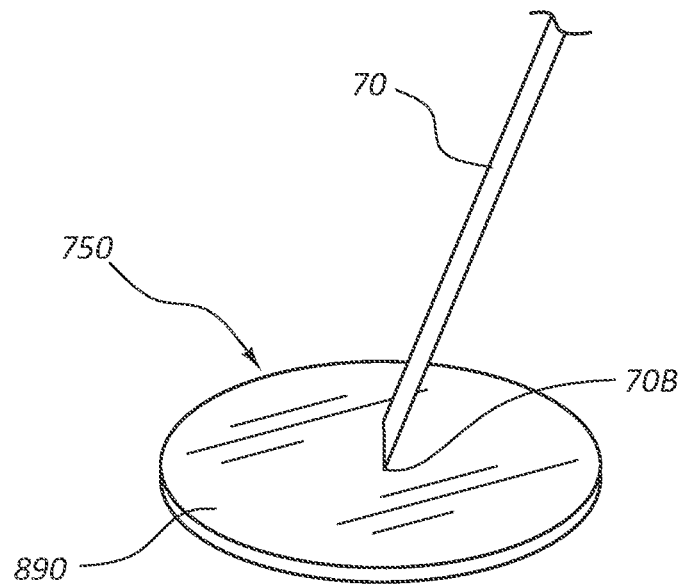
FIGS. 25A and 25B are various views of a needle stop feature according to one embodiment.
Figure 25B:
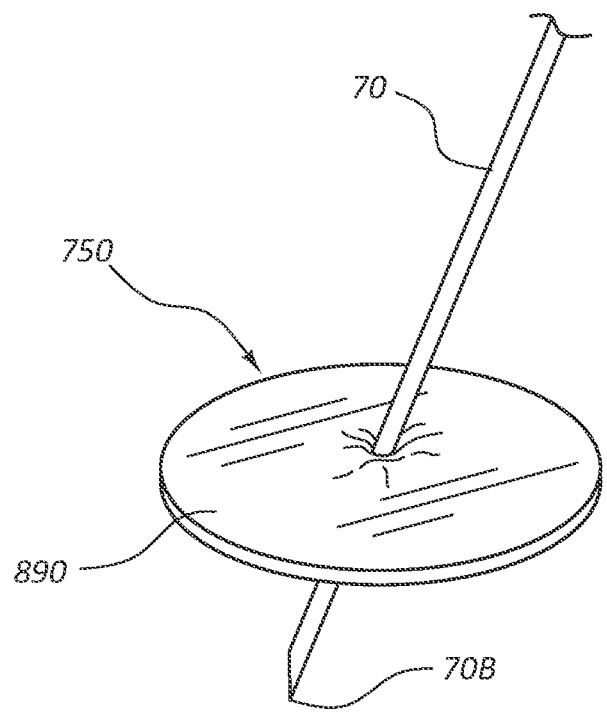

FIG. 25 gives another example of a needle lock feature 750 for preventing inadvertent contact or advancement of the needle 70, wherein a membrane 890 is placed in or over the guide channel, such as in the channel area 414 shown in FIGS. 14A and 14B. The membrane 890 in the present embodiment is sufficiently strong so as to prevent passage of the distal tip of the needle 70 therethrough when the needle is placed into contact therewith. Thus, the membrane 890 can be placed at or near a distal end of the guide channel to hold the needle in position within the channel. The membrane 890 is further configured to be pierceable by the distal tip 70B of the needle 70 upon application of a suitable amount of user force. Thus, when ready to advance the needle 70 into the patient, the clinician can apply force to the needle and cause it to pierce the membrane 890. Advancement of the needle 70 can then proceed as usual. In one embodiment, the membrane includes a suitable material, including silicone or other suitable plastic, metal, paper, etc. In one embodiment, the membrane, together with the needle guide assembly of which it is a part, is sterilizable.

Figure 26A:
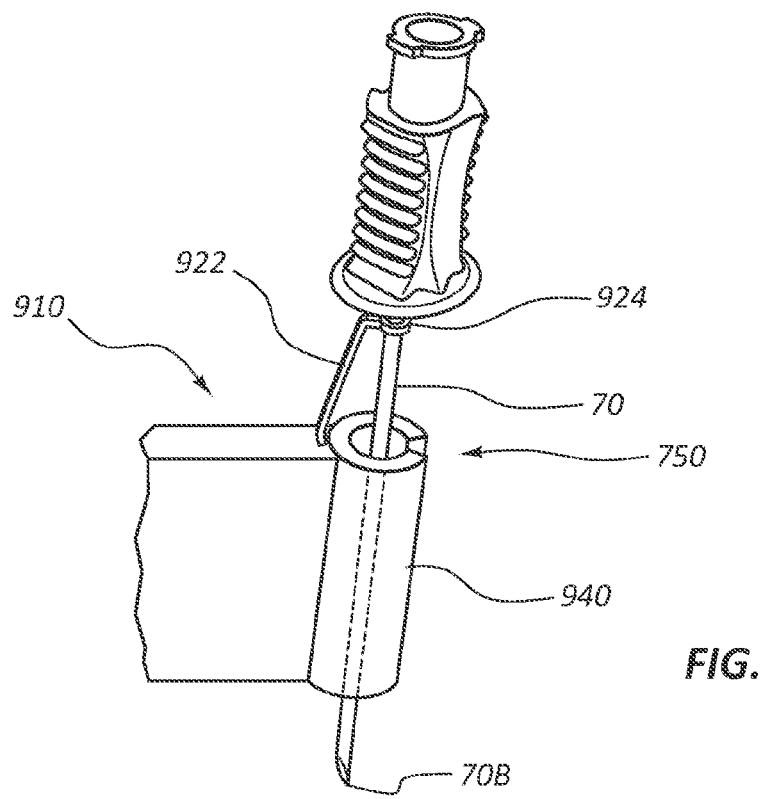
FIGS. 26A and 26B are various views of a needle stop feature according to one embodiment.
Figure 26B:
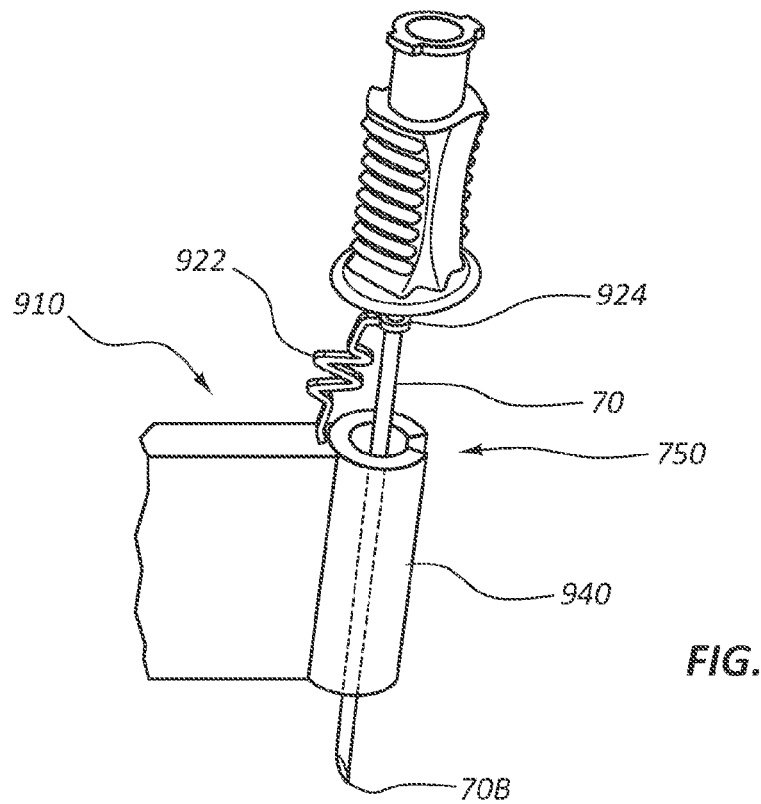

FIGS. 26A and 26B give another example of a needle guide assembly 910 including the needle lock feature 750 for preventing inadvertent contact or advancement of the needle 70. In the present embodiment, the needle lock feature 750 includes a collapsible arm 922 that attaches to the needle guide assembly 910 and extends toward the proximal end 70A of the needle. The arm 922 includes a collar 924 or other suitable component for supporting a hub of the needle 70. So configured, the arm 922 maintains the needle 70 in an un-advanced position after receipt of the needle within a guide channel 940 of the needle guide assembly 910.

As seen in FIG. 26B, the arm 922 is foldable or collapsible upon application of a sufficient amount of distal force thereon by a clinician. Upon application of the force, the arm 922 in the present embodiment is configured to fold up or collapse, thus enabling distal advancement of the needle 70. It is appreciated that the arm can be configured to collapse or fold in any number of ways, including longitudinally along the axis of the support, in a corrugating fashion, etc. Also, more than one support arm can be included or be differently shaped from what is shown and described.

FIGS. 27A and 27B show details of needle stop feature 750 according to another embodiment, wherein the feature includes a two-piece slide arm 952 that is slidably extensible so that the total height thereof can be selected and changed. This enables the needle stop feature to be employed with needles of different lengths. The slide arm 952 further includes a needle support 954 for supporting a hub or other proximal portion of the needle 70. As shown in FIG. 27B, the slide arm 952 can include demarcations to assist the clinician in selecting the proper height for a particular needle. The slide arm 952, when disposed on the needle guide assembly 910 as shown in FIG. 27A, supports the needle 70 in place within the guide channel 940 until user force is applied to collapse the two-piece slide arm and enable the needle to be distally advanced.

Optionally, the support structures of FIGS. 26A-27B can be used to set the needle position within the guide channel such that the needle distal tip is positioned a suitable distance above the skin. In the embodiment of FIGS. 27A and 27B, the demarcations can designate the total length of the needle. Thus, a clinician in one instance can adjust the support structure slide arm 952 until the needle length is displayed, attach the arm to the needle guide assembly 910, position the needle until the hub thereof is proximate the top of the needle support 954 of the slide arm 952 (which indicates that the distal tip of the needle is positioned a sufficient distance above the patient skin), then remove the support structure from the needle guide when distal advancement is desired.

FIG. 28 gives another example of a needle lock feature for preventing inadvertent contact or advancement of the needle 70, wherein a capture post 970 extends from a needle guide assembly, such as those described above, so as to enter into a distal opening 972 of a lumen 974 of the needle when the needle is disposed in the guide channel of the needle guide assembly. In particular, the capture post 970 is configured in one embodiment to engage the lumen distal opening 972 when the distal portion of the needle 660 extends distally from the guide channel. Capture of the lumen distal opening 972 in this manner prevents damage to the distal tip 70B of the needle 70, thus preserving its sharpness for insertion into the patient's skin. When distal advancement of the needle 70 is desired, the capture post 970 can be retracted from the distal opening 972 of the lumen 974 manually or via a mechanism attached thereto. Distal needle advancement can then proceed.

Figure 29:
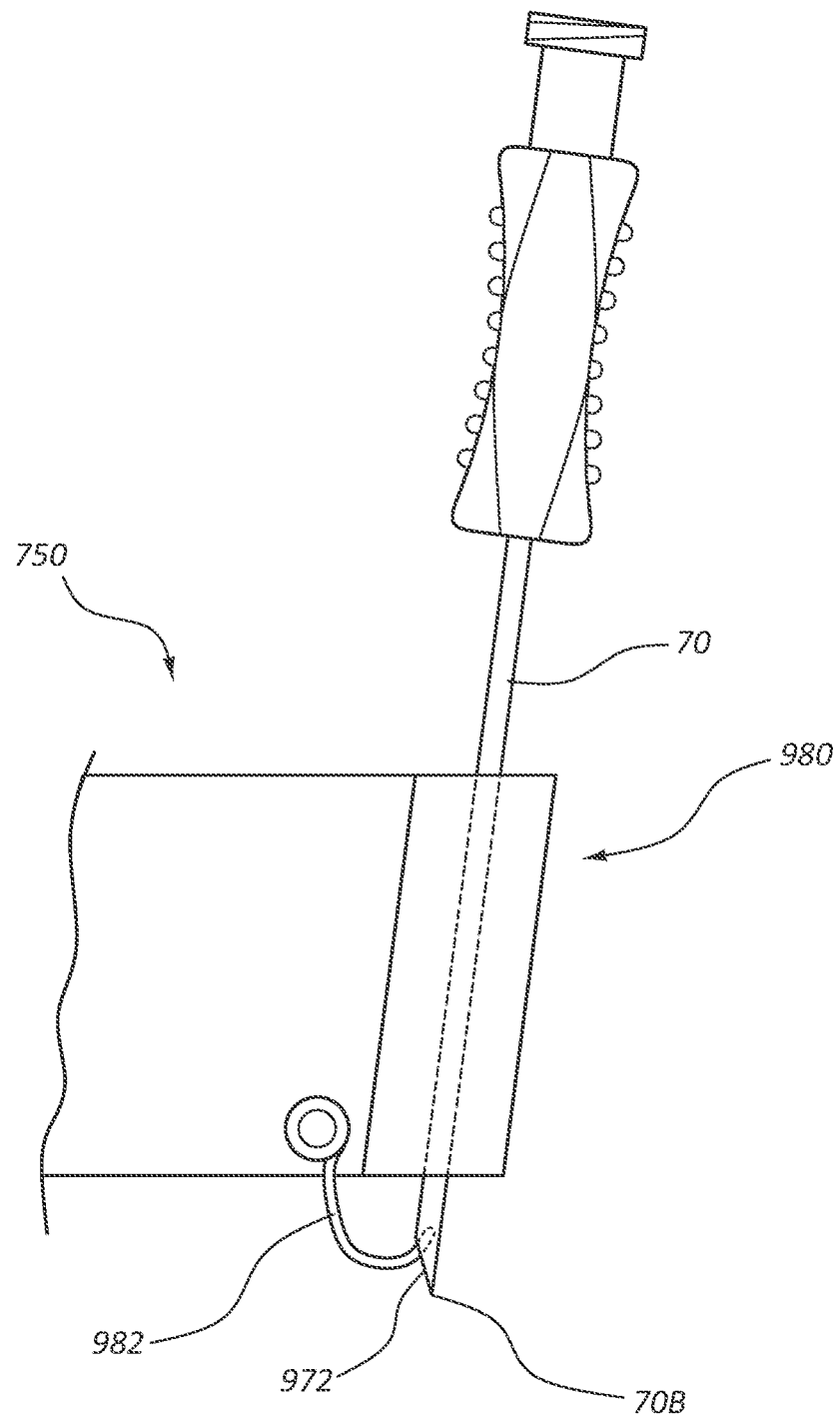
FIG. 29 is a view of a needle stop feature according to one embodiment.
Figure 30A:
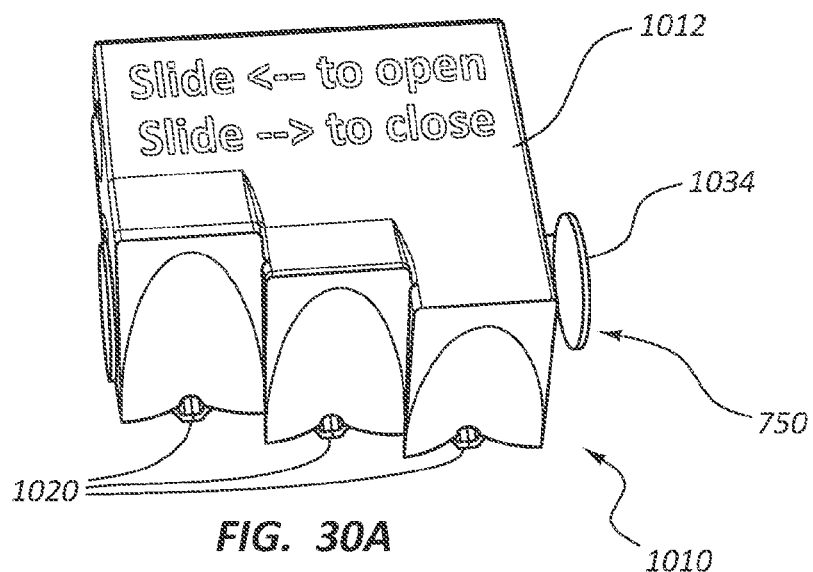
FIGS. 30A-31B show various views of a needle guide assembly including a needle stop feature according to one embodiment.
Figure 30B:
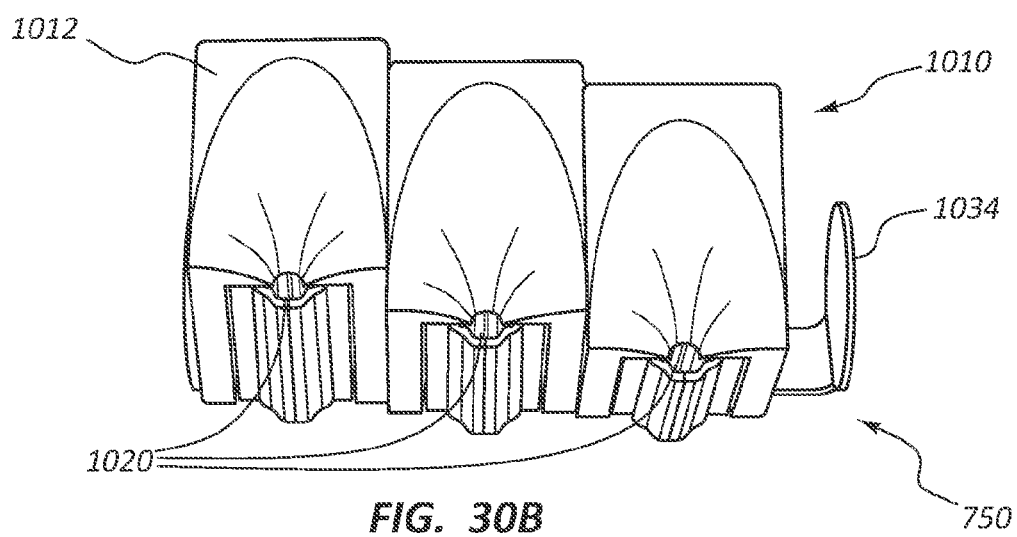
Figure 30C:
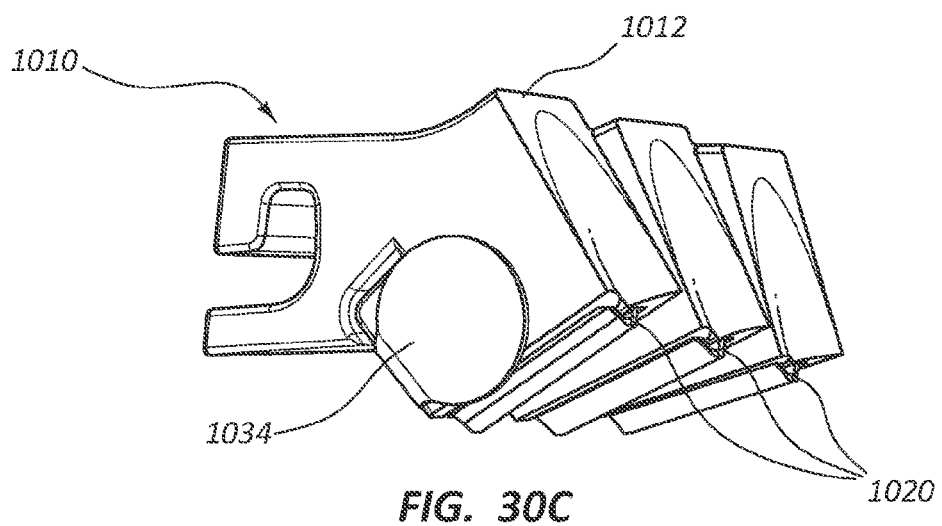

FIG. 29 provides an optional variation to the configuration described immediately above, wherein a capture hook 982 is included with a needle guide assembly 980. The capture hook 982 is configured to selectively engage the distal opening 972 of the lumen 974 of the needle 70 in a manner similar to that described for the capture post 970 of FIG. 28. Again, the capture hook 982 desirably prevents any damage to the distal tip 70B of the needle. Distal advancement of the needle can proceed after removing the capture hook 982 from the needle distal opening 972 via manual or other suitable applied force.

Figure 31A:
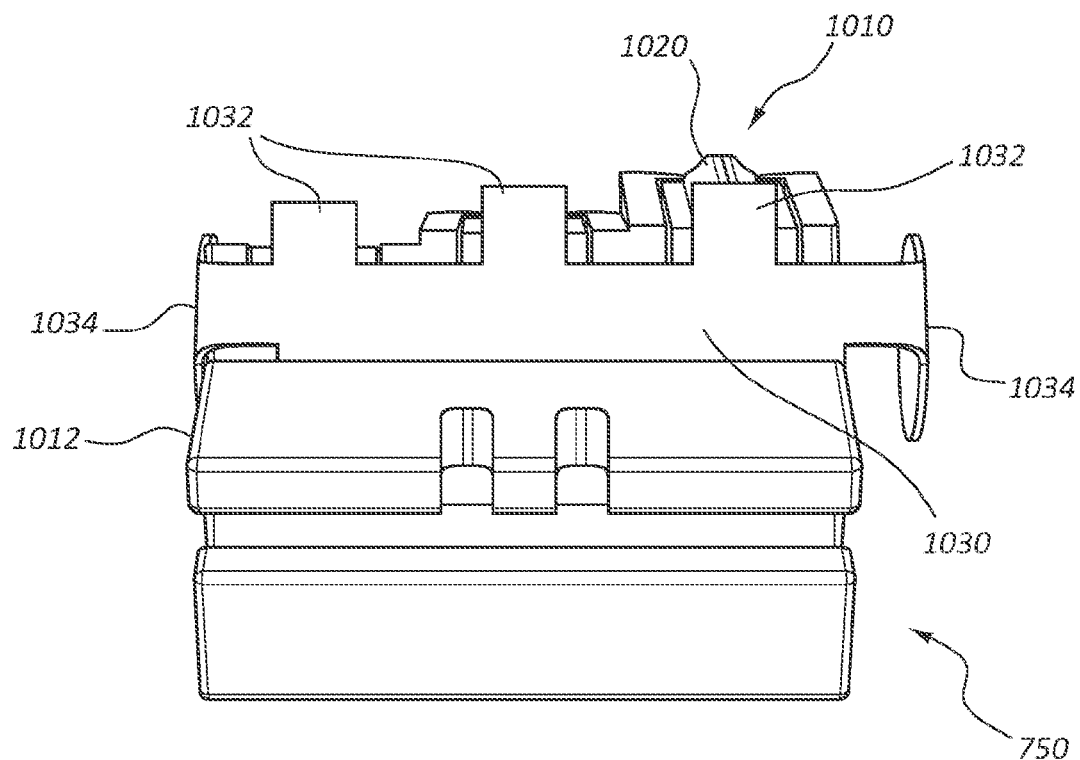
Figure 31B:
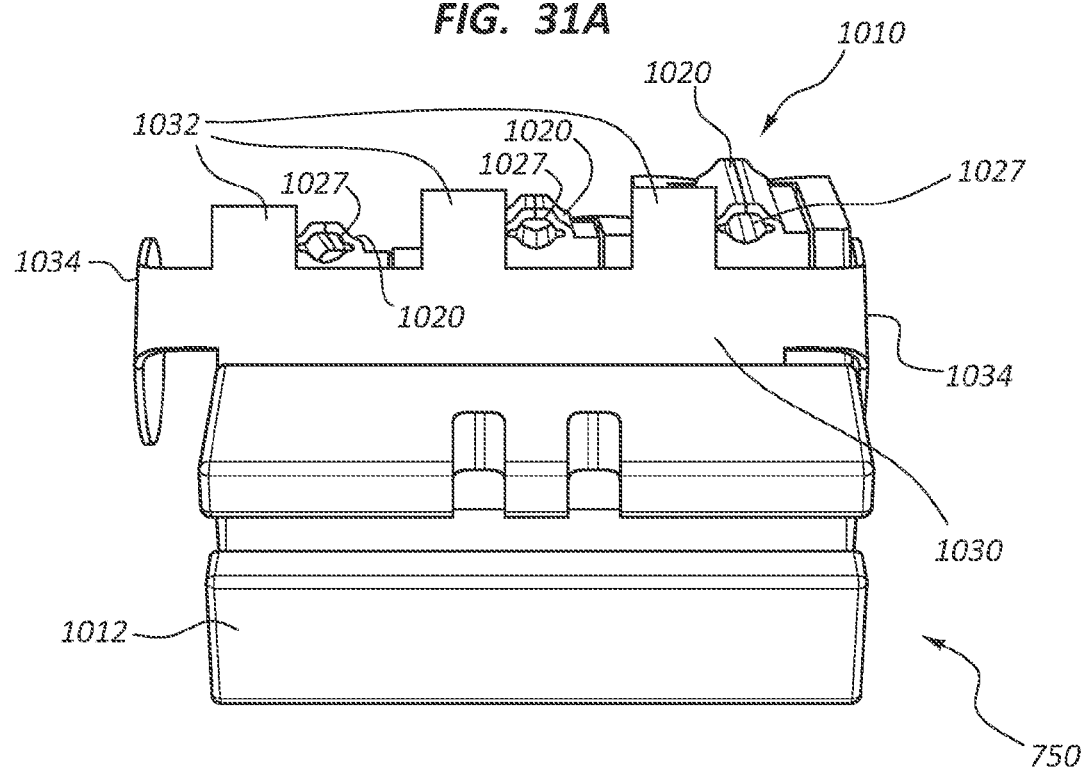

FIGS. 30A-31B give another example of a needle guide assembly 1010 that includes a needle lock feature 750 for preventing inadvertent contact or advancement of the needle 70, wherein the lock feature includes a lock feature body 1030 that is slidably attached to the needle guide assembly body 1012. The lock feature body 1030 includes a plurality of tabs, or shutters 1032, which are each configured to selectively cover the distal ends 1027 of each of the guide channels 1020 included on the needle guide assembly 1010. As shown in FIG. 31A, when the lock feature body 1030 is in a first position the three shutters 1032 cover the three distal ends 1027 of the guide channels 1020, thus preventing needle advancement therethrough. When the lock feature body 1030 is slid to a second position, as shown in FIG. 31B, the shutters 1032 are disposed to the side of the distal ends 1027, thus enabling needle passage through any one of the guide channels 1020. Note that press surfaces 1034 are included on either end of the lock feature body 1030 to facilitate sliding thereof by the clinician. Other suitable engagement surfaces can also be employed.

Figure 32A:
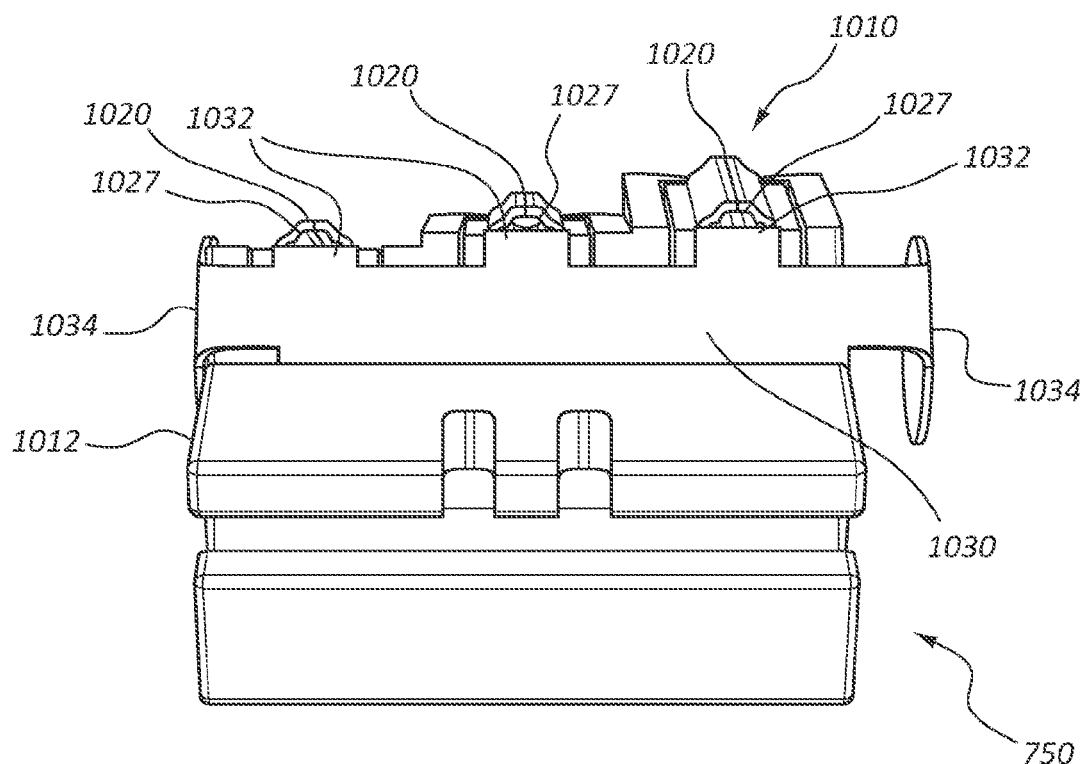
FIGS. 32A and 32B show various views of a needle guide assembly including a needle stop feature according to one embodiment.
Figure 32B:
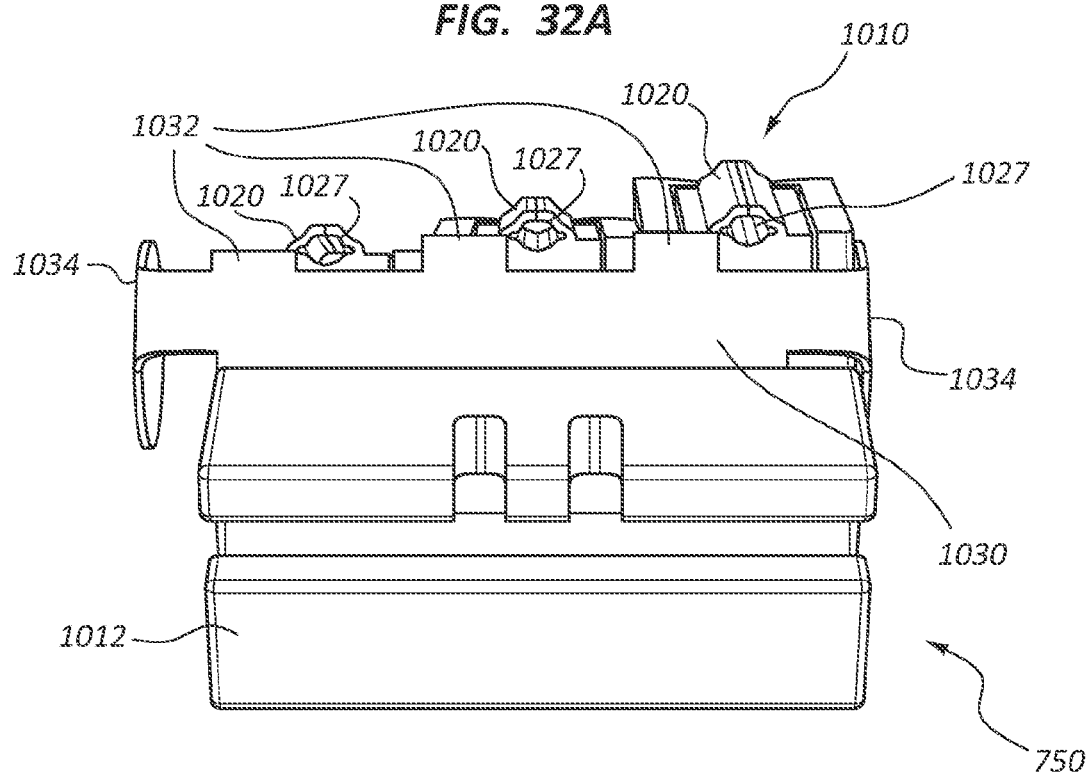

FIGS. 32A and 32B depict the needle lock feature 750 according to one embodiment, wherein the shutters 1032 included on the sliding lock feature body 1030 are sized so as to intercept only a proximal portion of a distal opening of the needle lumen (see, e.g., FIGS. 28, 29) such that the shutters do not contact the distal tip of the needle when they are selectively disposed over the distal ends 1027 of the guide channels 1020, as shown in FIG. 32A.

Figure 33A:
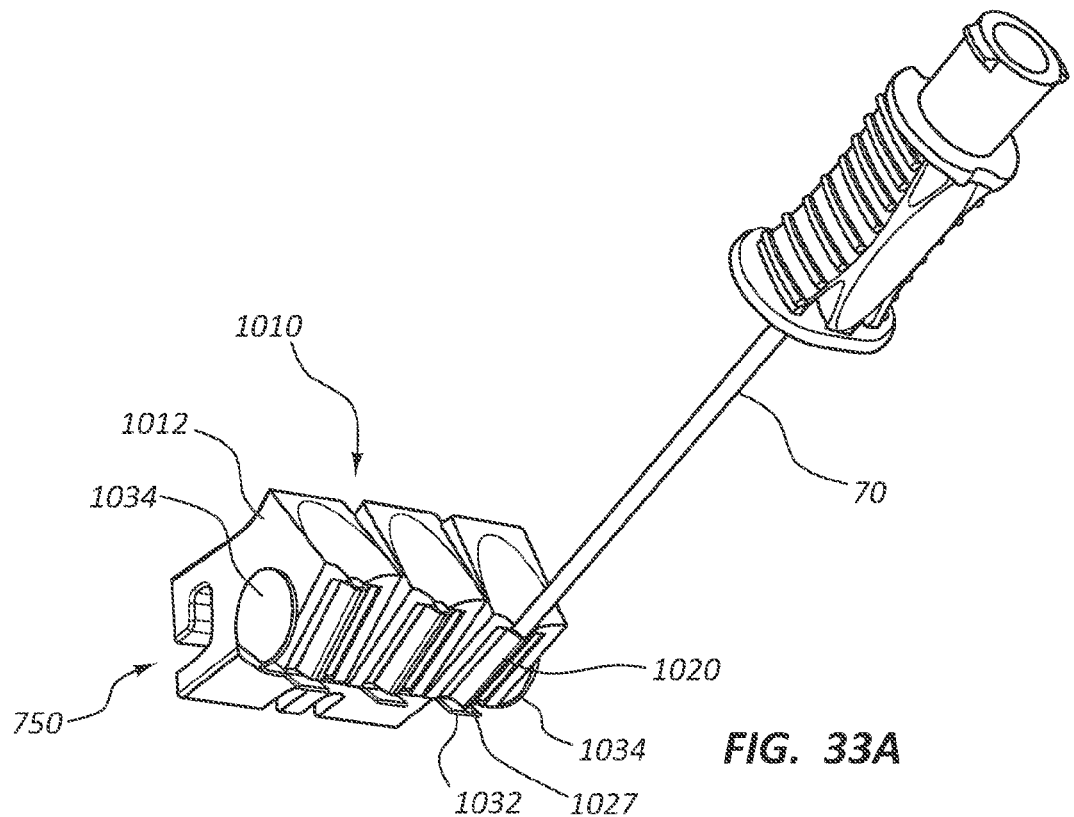
FIGS. 33A and 33B show various views of use of the needle guide assembly of FIGS. 30A-31B with a needle, according to one embodiment.
Figure 33B:
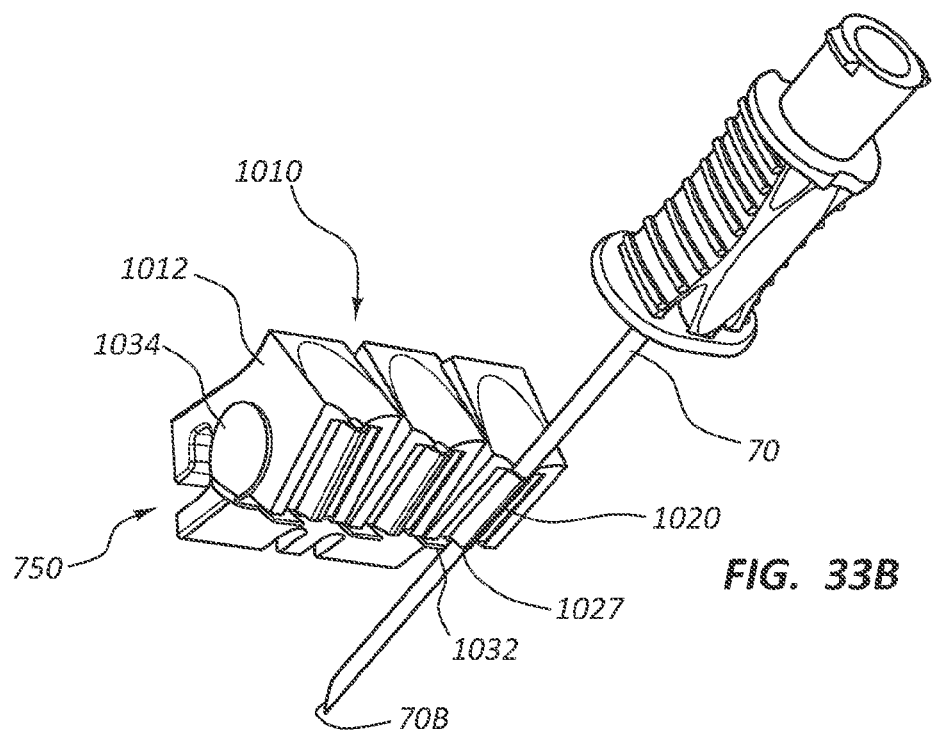

FIGS. 33A and 33B show advancement of the needle 70 through one of the guide channel 1020 of the needle guide assembly 1010 including the needle lock feature 750 as described in connection with FIGS. 30A-31B. In particular, FIG. 33A shows the lock feature body 1030 in the first position with the shutters 1032 thereof disposed over the distal ends 1027 of the guide channels 1020, thus preventing distal advancement of the needle 70. In contrast, FIG. 33B shows the lock feature body 1030 in the second position with the shutters 1032 disposed to the side of the guide channels 1020, thus enabling the needle 70 to pass therethrough.

The disclosure is not limited to the specific embodiments shown and described above. Note that the number of guide channels and corresponding shutters of the needle lock feature just described can vary. Also, the shape and configuration can vary to suit the particular design of the needle guide assembly.

More generally, in one possible embodiment a transparent guide channel structure can be employed to enable the clinician to observe the depth of needle penetration into the guide. In another possible embodiment, the guide channel can be colored a first color and the needle a second color. When the colored needle passes through the colored guide channel, the two colors interact and a third color is seen by the clinician, thus indicating to the clinician the position of the needle. For example, the guide channel can be colored yellow, and the needle blue. Upon passing the blue needle through the yellow guide channel, green is viewed by the clinician. In yet another embodiment, the needle guide can include a mark that will indicate to the clinician where advancement of the needle should be stopped to enable preparations for insertion of the needle into the patient to be made.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An assembly, comprising:
an ultrasound probe; and
a needle guide assembly, comprising:
   a plurality of guide channels, connected to a needle guide body, the needle guide body designed for attachment to the ultrasound probe, in each of the guide channels a needle can be temporarily disposed, the guide channels for guiding the needle into a patient; and
   a needle stop feature slidably engaged at a distal end of each of the plurality of guide channels, the needle stop feature remaining slidably engaged while being linearly movable between a first position for blocking the distal end of each of the guide channels and a second position where the needle stop feature enables needle passage through the guide channels.

2. The needle guide assembly as defined in claim 1, wherein the needle stop feature includes a plurality of shutters for covering the distal ends of each of the guide channels when the needle stop feature is in the first position.

3. The needle guide assembly as defined in claim 2, wherein the shutters in the first position are configured so as to engage only a portion of the needle proximal to the needle distal end when the needle is disposed in one of the guide channels so as to not blunt a distal tip of the needle.

4. The needle guide assembly as defined in claim 2, wherein the plurality of shutters covers only a portion of the distal ends of each of the guide channels when the needle stop feature is in the first position.

5. The needle guide assembly as defined in claim 2, wherein the plurality of shutters entirely covers the distal ends of each of the guide channels when the needle stop feature is in the first position.

6. The needle guide assembly as defined in claim 2, wherein the plurality of shutters extend outwardly along one edge of the needle stop feature.

7. The needle guide assembly as defined in claim 1, wherein the plurality of guide channels are arranged on one side of the needle guide assembly.

8. The needle guide assembly as defined in claim 7, wherein the plurality of guide channels includes three distinct guide channels arranged on the same side of the needle guide assembly.

9. The needle guide assembly as defined in claim 1, further comprising a plurality of front faces proximate proximal ends of the plurality of guide channels, wherein each of the plurality of front faces includes a contour shaped to direct a tip of a needle into a guide channel of the plurality of guide channels.

10. The needle guide assembly as defined in claim 9, wherein each of the plurality of front faces is positioned at a different angle, and wherein the contour of each of the plurality of front faces is concavely shaped.

11. The needle guide assembly as defined in claim 9, wherein each of the plurality of front faces is positioned facing outwardly away from the ultrasound probe when attached to the ultrasound probe.

12. The needle guide assembly as defined in claim 11, wherein the press surfaces extend from a main body portion of the needle stop feature at an angle perpendicular to the main body portion of the needle stop feature.

13. The needle guide assembly as defined in claim 1, wherein the needle stop feature comprises press surfaces at both a proximal end and a distal end of the needle stop feature.

14. The needle guide assembly as defined in claim 1, wherein the needle guide assembly is configured to at least indirectly and removably attach to the ultrasound probe such that the needle guide assembly is slidable laterally across a surface of the ultrasound probe.

15. The needle guide assembly as defined in claim 1, wherein each of the plurality of guide channels includes two compliant arms that together define an elongate volume into which the needle is inserted, each arm being movable upon needle insertion to increase size of the volume when necessary to enable passage of the needle.

16. The needle guide assembly as defined in claim 15, wherein each of the compliant arms of each of the plurality of guide channels includes a notch to facilitate compliant expansion of the elongate volume of the respective guide channel, and wherein a longitudinal slot is defined between the compliant arms of each of the plurality of guide channels to enable the needle to be removed from the needle guide assembly after needle insertion into a body of the patient.

17. The needle guide assembly as defined in claim 1, wherein the needle guide assembly is slidably attachable to a cap that is removably attached to a head portion of the ultrasound probe.

18. An assembly comprising:
an ultrasound probe; and
a needle guide assembly, comprising:
   a plurality of guide channels, connected to a needle guide body, the needle guide body designed for attachment to an ultrasound probe, the plurality of guide channels designed for guiding a needle into a patient; and
   a needle stop designed to transition the plurality of guide channels from an open position to a closed position, the needle stop blocking a distal end of each of the guide channels in the closed position, the needle stop linearly slidable between the open and closed positions and attached to the needle guide in both the open and closed positions.

* * * * *